(12) United States Patent
Neumann

(10) Patent No.: US 11,594,333 B2
(45) Date of Patent: Feb. 28, 2023

(54) DEVICE AND METHODS OF CALCULATING A THERAPEUTIC REMEDY RESULT

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 277 days.

(21) Appl. No.: 17/007,205

(22) Filed: Aug. 31, 2020

(65) Prior Publication Data
US 2021/0098130 A1 Apr. 1, 2021

Related U.S. Application Data

(63) Continuation-in-part of application No. 16/589,061, filed on Sep. 30, 2019, now Pat. No. 10,832,822.

(51) Int. Cl.
| | | |
|---|---|---|
| *G16H 50/20* | (2018.01) | |
| *G16H 50/70* | (2018.01) | |
| *G16H 40/67* | (2018.01) | |
| *A61B 5/00* | (2006.01) | |
| *G16H 10/60* | (2018.01) | |
| *G16H 50/30* | (2018.01) | |

(52) U.S. Cl.
CPC .......... *G16H 50/20* (2018.01); *A61B 5/4848* (2013.01); *A61B 5/6801* (2013.01); *A61B 5/742* (2013.01); *G16H 10/60* (2018.01); *G16H 40/67* (2018.01); *G16H 50/30* (2018.01); *G16H 50/70* (2018.01)

(58) Field of Classification Search
CPC ........ G16H 50/20; G16H 40/67; G16H 10/60; G16H 50/30; G16H 50/70; A61B 5/4848; A61B 5/6801; A61B 5/742
USPC .......................................................... 705/2–3
See application file for complete search history.

(56) References Cited

U.S. PATENT DOCUMENTS

| | | |
|---|---|---|
| 7,418,399 B2 | 8/2008 | Schaeffer et al. |
| 7,880,751 B2 | 2/2011 | Kuo et al. |
| 7,899,764 B2 | 3/2011 | Martin et al. |
| 8,095,384 B2 | 1/2012 | Firminger et al. |
| 8,655,817 B2 * | 2/2014 | Hasey ...................... A61B 5/00 706/45 |

(Continued)

OTHER PUBLICATIONS

Chen et al.; "A Disease Diagnosis and Treatment Recommendation System Based on Big Data Mining and Cloud Computing"; Oct. 19, 2018; https://arxiv.org/pdf/1810.07762.pdf.

(Continued)

*Primary Examiner* — Michael Tomaszewski
(74) *Attorney, Agent, or Firm* — Caldwell Intellectual Property Law

(57) ABSTRACT

A device for calculating a therapeutic remedy result, the device including a display; a sensor; and a computing device in communication with the display and the sensor, wherein the computing device is configured to record a user vibrancy datum; identify a therapeutic remedy instruction set as a function of the user vibrancy datum, wherein the therapeutic remedy instruction set comprises a therapeutic remedy; and calculate a therapeutic remedy result that associates the user vibrancy datum and the therapeutic remedy with a therapy response curve.

20 Claims, 13 Drawing Sheets

(56) References Cited

U.S. PATENT DOCUMENTS

| | | | |
|---|---|---|---|
| 9,460,400 B2 | 10/2016 | De Bruin et al. | |
| 10,073,951 B2 | 9/2018 | Mohebbi et al. | |
| 2009/0246171 A1* | 10/2009 | Van Antwerp | G16H 20/17 424/85.4 |
| 2019/0117978 A1* | 4/2019 | Arcot Desai | A61N 1/36139 |
| 2019/0198169 A1* | 6/2019 | T | G16H 50/50 |

OTHER PUBLICATIONS

Nezhad, Milad Zafar; "Data-Driven Modeling for Decision Support Systems and Treatment Management in Personalized Healthcare"; Jan. 1, 2018; https://digitalcommons.wayne.edu/cgi/viewcontent.cgi?article=3082&context=oa_dissertations.

Mccallum et al.; "Efficient Clustering of High-Dimensional Data Sets With Appliation to Reference Matching"; 2000; http://citeseerx.ist.psu.edu/viewdoc/download?doi=10.1.1.561.9145&rep=rep1&type=pdf.

* cited by examiner

US 11,594,333 B2

DEVICE AND METHODS OF CALCULATING A THERAPEUTIC REMEDY RESULT

RELATED APPLICATION DATA

This application is a continuation-in-part of U.S. patent application Ser. No. 16/589,061, filed on Sep. 30, 2019 which is hereby incorporated by reference herein in its entirety.

FIELD OF THE INVENTION

The present invention generally relates to the field of artificial intelligence. In particular, the present invention is directed to a device and methods of calculating a therapeutic remedy result.

BACKGROUND

Locating therapeutic remedies that have been successful for individuals with shared medical conditions can be challenging. Therapeutic professionals are often overwhelmed with the quantity of literature to evaluate. Further, novel therapeutic remedies and medical conditions are created every day.

SUMMARY OF THE DISCLOSURE

In an aspect, a device for calculating a therapeutic remedy result includes a display, a sensor, and a computing device in communication with the display and the sensor. The computing device is configured to record a user vibrancy datum, identify a therapeutic remedy instruction set as a function of the user vibrancy datum, wherein the therapeutic remedy instruction set includes a therapeutic remedy, calculate a therapeutic remedy result that associates the user vibrancy datum and the therapeutic remedy with a therapy response curve, wherein calculating the therapeutic remedy result further comprises receiving therapy training data, wherein therapy training data further comprises a plurality of data entries containing user vibrancy datums and therapeutic remedy instruction sets correlated to therapeutic remedy results, training a therapy machine learning process using the therapy training data, wherein the therapy machine learning process uses the user vibrancy datum and the therapeutic remedy as an input, and outputs a therapy response curve and a therapeutic remedy result, and generating the therapeutic remedy result as a function of training the therapy machine learning process.

In an aspect, a method of calculating a therapeutic remedy result includes recording, by a device, a user vibrancy datum, identifying, by the device, a therapeutic remedy instruction set as a function of the user vibrancy datum, wherein the therapeutic remedy instruction set comprises a therapeutic remedy, and calculating by the device, a therapeutic remedy result that associates the user vibrancy datum and the therapeutic remedy with a therapy response curve. Calculating the therapeutic remedy result includes receiving therapy training data, wherein therapy training data further comprises a plurality of data entries containing user vibrancy datums and therapeutic remedy instruction sets correlated to therapeutic remedy results, training a therapy machine learning process using the therapy training data, wherein the therapy machine learning process uses the user vibrancy datum and the therapeutic remedy as an input, and outputs a therapy response curve and a therapeutic remedy result, and generating the therapeutic remedy result as a function of training the therapy machine learning process.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for locating therapeutic remedies. In an embodiment, a system for locating therapeutic remedies. The system includes a k-means clustering module that is configured to receive at least a therapeutic constitutional inquiry. The k-means clustering module is configured to locate a user vibrancy record containing a plurality of user vibrancy datums stored in a vibrancy database. The k-means clustering module is configured to select at least a user vibrancy datum as a function of at least a therapeutic constitutional inquiry. The k-means clustering module is configured to receive a clustering dataset containing a plurality of unclassified cluster data entries. The k-means clustering module is configured to generate a k-means clustering algorithm using the clustering dataset. The k-means clustering module is configured to calculate a degree of similarity index value that includes a distance measurement between a classified data entry cluster and a selected user vibrancy datum. The k-means clustering module is configured to select a classified data entry cluster as a function of the degree of similarity index value. The system includes a k-nearest neighbors module that is configured to generate a k-nearest neighbors algorithm utilizing the selected data entry cluster. The k-nearest neighbors module is configured to identify at least a therapeutic dataset contained within a selected classified data entry cluster. The k-nearest neighbors module is configured to generate a therapeutic remedy instruction set and display the therapeutic remedy instruction set on a graphical user interface.

Figure 1:
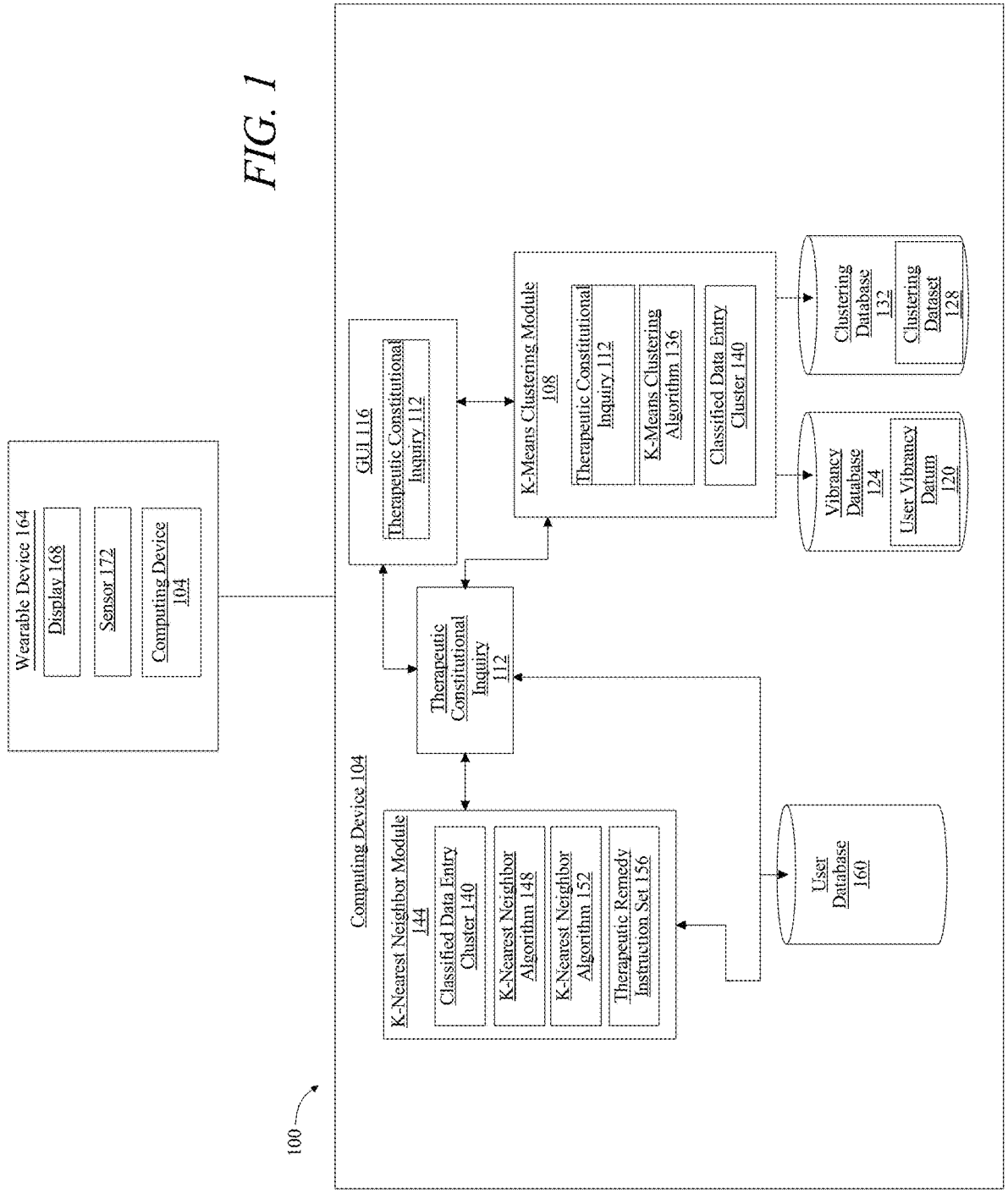
FIG. 1 is a block diagram illustrating an exemplary embodiment of a system for locating therapeutic remedies.

Referring now to FIG. 1, an exemplary embodiment of a system 100 for locating therapeutic remedies. System 100 includes at least a computing device 104, wherein the at least a computing device 104 further comprises one or more network interfaces, a non-volatile memory, and including one or more processors. Computing device 104, as used herein, includes any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include at least a server. At least a server may include a single computing device 104 operating independently or may include two or more computing device 104 operating in concert, in parallel, sequentially or the like; two or more computing device 104 may be included together in a single computing device 104 or in two or more computing device 104. At least a server may interact with one or more additional devices as described below in further detail via a network interface device. Network interface device may be utilized for connecting at least a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104, and any combinations thereof. A network may employ a wired and/or a wireless mode of communication. In general, any network topology may be used. Information (e.g., data, software etc.) may be communicated to and/or from a computer and/or a computing device 104. At least a server may include but is not limited to, for example, a computing device 104 or cluster of computing device 104 in a first location and a second computing device 104 or cluster of computing device 104 in a second location. At least a server may include one or more computing device 104 dedicated to data storage, security, distribution of traffic for load balancing, and the like. At least a server may distribute one or more computing tasks as described below across a plurality of computing device 104 of computing device 104, which may operate in parallel, in series, redundantly, or in any other manner used for distribution of tasks or memory between computing device 104. At least a server may be implemented using a "shared nothing" architecture in which data is cached at the worker, in an embodiment, this may enable scalability of system 100 and/or computing device 104.

With continued reference to FIG. 1, at least a computing device 104 may be designed and/or configured to perform any method, method step, or sequence of method steps in any embodiment described in this disclosure, in any order and with any degree of repetition. For instance, at least a computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a k-means clustering module 108 operating on at least a computing device. K-means clustering module 108 may include any hardware and/or software module. K-means clustering module 108 is designed and configured to receive at least a therapeutic constitutional inquiry 112 from a graphical user interface 116 by a therapeutic professional wherein the at least a therapeutic constitutional inquiry 112 includes a user identifier; locate a user vibrancy record containing a plurality of user vibrancy datum 120 stored in a database as a function of the user identifier; select at least a user vibrancy datum 120 as a function of the at least a therapeutic constitutional inquiry 112; receive a clustering dataset 128 wherein the dataset further comprises a plurality of unclassified cluster data entries; generate a k-means clustering algorithm 136 using the clustering dataset 128 containing the plurality of cluster data entries containing unclassified data as input and wherein the k-means clustering algorithm 136 outputs a definite number of classified data entry cluster 140 wherein the data entry clusters each contain cluster data entries; calculate a degree of similarity index value wherein the degree of similarity index value further comprises a measurement distance between a data entry cluster and the at least a selected user vibrancy datum 120; and select a classified data entry cluster 140 as a function of the degree of similarity index value.

With continued reference to FIG. 1, k-means clustering module 108 is configured to receive at least a therapeutic constitutional inquiry 112 from a graphical user interface 116 by a therapeutic professional wherein the at least a therapeutic constitutional inquiry 112 includes a user identifier. A "therapeutic constitutional inquiry 112" as used in this disclosure, includes data describing a current diagnosed medical condition that a patient has been diagnosed with by a therapeutic professional. Medical condition may include a particular disease, one or more symptoms associated with a syndrome, a syndrome, and/or any other measure of current or future health and/or healthy aging. Conditions associated with therapeutic constitutional inquiry 112 may include, without limitation one or more diseases, defined for purposes herein as conditions that negatively affect structure and/or function of part or all of an organism. Conditions associated with therapeutic constitutional inquiry 112 may include, without limitation, acute or chronic infections, including without limitation infections by bacteria, archaea, viruses, viroid, prions, single-celled eukaryotic organisms such as amoeba, paramecia, trypanosomes, plasmodia, leishmania, and/or fungi, and/or multicellular parasites such as nematodes, arthropods, fungi, or the like. Therapeutic constitutional inquiry 112 may be associated with one or more immune disorders, including without limitation immunodeficiencies and/or auto-immune conditions. Therapeutic constitutional inquiry 112 may be associated with one or more metabolic disorders. Therapeutic constitutional inquiry 112 may be associated with one or more endocrine disorders. Therapeutic constitutional inquiry 112 may be associated with one or more cardiovascular disorders. Therapeutic constitutional inquiry 112 may be associated with one or more respiratory disorders. Therapeutic constitutional inquiry 112 may be associated with one or more disorders affecting connective tissue. Therapeutic constitutional inquiry 112 may be associated with one or more digestive disorders. Therapeutic constitutional inquiry 112 may be associated with one or more neurological disorders such as neuromuscular disorders, dementia, or the like. Therapeutic constitutional inquiry 112 may be associated with one or more disorders of the excretory system, including without limitation nephrological disorders. Therapeutic constitutional inquiry 112 may be associated with one or more liver disorders. Therapeutic constitutional inquiry 112 may be associated with one or more disorders of the bones such as osteoporosis. Therapeutic constitutional inquiry 112 may be associated with one or more disorders affecting joints, such as osteoarthritis, gout, and/or rheumatoid arthritis. Therapeutic constitutional inquiry 112 be associated with one or more cancers, including without limitation carcinomas, lymphomas, leukemias, germ cell tumor cancers, blastomas, and/or sarcomas. Therapeutic constitutional inquiry 112 may include descriptors of latent, dormant, and/or apparent disorders, diseases, and/or conditions. Therapeutic constitutional inquiry 112 may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with therapeutic constitutional inquiry 112 as described in this disclosure.

Still referring to FIG. 1, at least a therapeutic constitutional inquiry 112 may be stored in any suitable data and/or data type. For instance, and without limitation, at least a therapeutic constitutional inquiry 112 may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a therapeutic constitutional inquiry 112 may take; persons skilled in the art, upon reviewing the entirety of this disclosure, will be aware of various forms which may be suitable for use as at least a therapeutic constitutional inquiry 112 consistently with this disclosure.

With continued reference to FIG. 1, therapeutic constitutional inquiry 112 is input from a graphical user interface 116. Graphical user interface 116 may include without limitation, a form or other graphical element having data entry fields, wherein a therapeutic professional may enter a therapeutic constitutional inquiry 112. Graphical user interface 116 may include data entry fields that allow for a user to enter free form textual inputs describing a therapeutic constitutional inquiry 112. Graphical user interface 116 may provide drop-down lists, where users such as therapeutic professionals may be able to select one or more entries to indicate one or more therapeutic constitutional inquiries.

With continued reference to FIG. 1, therapeutic constitutional inquiry 112 is generated by a therapeutic professional. A "therapeutic professional" as used in this disclosure, includes a person who is licensed by a state and/or federal licensing agency that may help in identifying, preventing, and/or treating illness and/or disability. A therapeutic professional may include persons such as a functional medicine doctor, a doctor of osteopathy, a nurse practitioner, a physician assistant, a Doctor of Optometry, a doctor of dental medicine, a doctor of dental surgery, a naturopathic doctor, a doctor of physical therapy, a nurse, a doctor of chiropractic medicine, a doctor of oriental medicine, and the like. A therapeutic professional may include persons such as nurses, respiratory therapists, pharmacists, home health aides, audiologist, clinical nurse specialist, audiologist, nutritionist, dietician, clinical psychologists, psychiatric mental health nurse practitioners, and the like.

With continued reference to FIG. 1, therapeutic constitutional inquiry 112 input includes a user identifier. A "user identifier" as used in this disclosure, includes a unique identifier containing a series of numbers and/or letters that may uniquely identify a particular patient without disclosing a patient's name. For instance and without limitation, a user identifier may include a medical record number which may include a unique series of numbers that may be utilized to retrieve a patient's record.

With continued reference to FIG. 1, k-means clustering module 108 is configured to locate a user vibrancy record containing a plurality of user vibrancy datum 120 stored in a database as a function of the user identifier. A "user vibrancy record" as used in this disclosure, is an electronic medical chart. An electronic medical chart may contain a record of a patient's key clinical data, medical history, lab results, vital signs, diagnoses, medications, treatment plans, progress notes, problems, immunization dates, allergies, radiology images, and the like. K-means clustering module 108 may locate a user vibrancy record by searching for a user identifier. In an embodiment, k-means clustering module 108 may match a user identifier contained within a therapeutic constitutional inquiry 112 to a user identifier contained within a user vibrancy record. User identifiers that are equivalent may belong to the same patient. User identifiers that are not equivalent may not belong to the same patient. User vibrancy record may contain a plurality of user vibrancy datum 120. A "user vibrancy datum 120" as used in this disclosure, includes data describing a component of a user vibrancy record. For instance and without limitation, a user vibrancy datum 120 may include all immunization records for a patient. In yet another non-limiting example, a user vibrancy datum 120 may be filtered to only contain immunization records for a patient during a specific time period of the patient's life or only for a particular immunization such as tetanus.

With continued reference to FIG. 1, system 100 may include a vibrancy database 124. Vibrancy database 124 may include any data structure for ordered storage and retrieval of data, which may be implemented as a hardware or software module. Vibrancy database 124 may be implemented, without limitation, as a relational database, a key-value retrieval datastore such as a NOSQL database, or any other format or structure for use as a datastore that a person skilled in the art would recognize as suitable upon review of the entirety of this disclosure. Vibrancy database 124 may include data entries as described in more detail below. K-means clustering module 108 selects at least a user vibrancy datum 120 as a function of at least a therapeutic constitutional inquiry 112. In an embodiment, therapeutic constitutional inquiry 112 may indicate which user vibrancy datum 120 is related to and/or relevant to a particular therapeutic constitutional inquiry 112. For instance and without limitation, a therapeutic constitutional inquiry 112 such as rheumatoid arthritis may be relevant to a user vibrancy datum 120 containing a lab work showing an elevate erythrocyte sedimentation rate (ESR). In yet another non-limiting example, a therapeutic constitutional inquiry 112 such as heart disease may be relevant to a genetic test showing confirming the presence of apolipoprotein E4 gene. In an embodiment, a therapeutic professional may indicate through a graphical user interface 116 what user vibrancy datum 120 may be relevant. In yet another embodiment, K-means clustering module 108 may determine which vibrancy datums may be relevant to a particular therapeutic constitutional inquiry 112 based on learned associations. K-means clustering module 108 may consult a list that may be stored within vibrancy database 124 that may list common associations between therapeutic constitutional inquiries and user vibrancy datum 120. K-means clustering module is configured to categorize at least a user vibrancy datum to a body location and select the at least a user vibrancy datum as a function of the body location. "Body location" as used in this disclosure includes a particular body part, body organ, muscle, tissue and/or body system impacted by a particular user vibrancy datum. For instance and without limitation, a headache may impact the frontal lobe of the head while endocarditis may impact heart muscle.

With continued reference to FIG. 1, K-means clustering module 108 is configured to receive a clustering dataset 128 wherein the clustering dataset 128 includes a plurality of unclassified cluster data entries. Dataset may be stored in any suitable data and/or data type. For instance and without limitation, dataset may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as dataset may take; persons skilled in the art, upon reviewing the entirety of this disclosure, will be aware of various forms which may be suitable for use as dataset consistently with this disclosure.

With continued reference to FIG. 1, dataset may be stored as image data, such as for example an image of a particular food substance such as a photograph of a pear or an image of a steak. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, datasets may be obtained from a plurality of sources. Datasets contained within clustering database 132 may contain a plurality of data entries, obtained for example, from patient medical records that have been stripped of identifying information. Datasets contained within body database may be obtained from patient surveys who may be sampled in a variety of methods such as by phone, mail, internet and the like. Patient surveys may be distributed to patients across a breadth of geographical locations and may also be stripped of identifying information. Datasets contained within clustering database 132 may be obtained from clinical data such as from facilities including nursing homes, hospitals, home health agencies, and the like.

With continued reference to FIG. 1, dataset may be stored in a clustering database 132. Clustering database 132 may include any database structure suitable for use as vibrancy database 124. Data entries contained within clustering dataset 128 include unclassified cluster data entries. "Unclassified cluster data entries" as used in this disclosure, include data entries that have not been assigned, generated, and/or calculated category labels. Classification may include the process of predicting a class of given data entries. Classification may include using predictive modeling that approximates a mapping function from input variables to discrete output variables. Classification may be performed utilizing classification algorithms that include for example decision trees, naïve bayes, artificial neural networks, boosting, kernel methods, and/or k-nearest neighbors algorithms.

With continued reference to FIG. 1, K-means clustering module 108 is configured to generate a k-means clustering algorithm 136 using the clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean. Cluster data entry may include data entries selected from a clustering dataset. Cluster data entry may be received from clustering database. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DB-SCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, k-means clustering module 108 generates a k-means clustering algorithm 136 containing unclassified data as input and outputs a definite number of classified data entry cluster 140 wherein the data entry clusters each contain cluster data entries. K-means clustering module 108 may select a specific number of groups or clusters to output, identified by the variable "k." Generating a k-means clustering algorithm 136 includes assigning inputs containing unclassified data to a "k-group" or "k-cluster" based on feature similarity. Centroids of k-groups or k-clusters may be utilized to generate classified data entry cluster 140. K-means clustering module 108 by select "k" variable by calculating k-means clustering algorithm 136 for a range of k values and comparing results. K-means clustering module 108 may compared results across different values of k as the mean distance between cluster data entries and cluster centroid. K-means clustering module 108 may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering module 108 may select a k value by classifying at least a therapeutic constitutional inquiry 112. K-means clustering module 108 may evaluate at least a therapeutic constitutional inquiry 112 to determine a constitutional classifier. A "constitutional classifier" as used in this disclosure, includes a label classifying a particular medical condition contained within a therapeutic constitutional inquiry to a particular disease classifier. A disease classifier may include classifying a medical condition by a particular classification system such as by body region or body system impacted by a medical condition, by anatomical classification such as by organ or tissue impacted by a particular medical condition, by etiological containing a cause for a particular medical condition, and/or by pathological containing a medical condition process. K-means clustering module 108 utilizes a constitutional classifier to select a definite number of classified data entry cluster 140 or k-value. In an embodiment, a particular constitutional classifier may indicate a preferred k-value based on previous data collections and calculations. For instance and without limitation, a constitutional classifier that indicates a body region such as the gastrointestinal system may be best suited for a k-value of 77 while a constitutional classifier that indicates a body region such as the left thumb may be best suited for a k-value of 14.

With continued reference to FIG. 1, generating a k-means clustering algorithm 136 includes generating initial estimates for k centroids which may be randomly generated or randomly selected from unclassified data input. K centroids may be utilized to define one or more clusters. K-means clustering module 108 may assign unclassified data to one or more k-centroids based on the squared Euclidean distance by first performing a data assigned step of unclassified data. K-means clustering module 108 may assign unclassified data to its nearest centroid based on the collection of centroids ci of centroids in set C. Unclassified data may be assigned to a cluster based on $$\underset{ci \ni C}{\operatorname{argmin}} \, dist(ci, x)^2,$$

where argmin includes argument of the minimum; ci includes a collection of centroids in a set C; and dist includes standard Euclidean distance. K-means clustering module 108 may then recompute centroids by taking mean of all cluster data entries assigned to a centroid's cluster. This may be calculated based on $ci=1/|Si|\Sigma xi \in Si^{xi}$. K-means clustering module 108 may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering module 108 is configured to calculate a degree of similarity index value. A "degree of similarity index value" as used in this disclosure, includes a distance measurement indicating a measurement between each data entry cluster generated by k-means clustering algorithm 136 and a selected user vibrancy datum 120. Degree of similarity index value may indicate how close a particular user vibrancy datum 120 is to being classified by k-means algorithm to a particular cluster. K-means clustering module 108 may evaluate the distances of the user vibrancy datum 120 to the k-number of clusters output by k-means clustering algorithm 136. Short distances between a user vibrancy datum 120 and a cluster may indicate a higher degree of similarity between a user vibrancy datum 120 and a particular cluster. Longer distances between a user vibrancy datum 120 and a cluster may indicate a lower degree of similarity between a user vibrancy datum 120 and a particular cluster. Degree of similarity index value may include calculating by k-means clustering module 108 a background factor multiplied by an age factor and a vibrancy factor and divided by a life value factor. A "background factor" as used in this disclosure, includes a numerical value indicating how similar background demographic details may be between demographic background information regarding a user and demographic background information pertaining to cluster data entries contained within a particular cluster. Demographic background information may include information relating to address, marital status, sex, race, religion, occupation, offspring, and the like. An "age factor" as used in this disclosure, includes a numerical value indicating how similar in age a user may be as compared to cluster data entries contained within a particular cluster. Age may include the length of time that a user has lived since being born. A "vibrancy factor" as used in this disclosure, includes a numerical value indicating how similar a user's medical condition may be as compared to cluster data entries contained within a particular cluster. Medical condition may include any of the medical conditions contained within a therapeutic constitutional inquiry 112 as described above. Vibrancy factor may include a disease score multiplied by a life year score. Disease score may include a numerical value indicating how severe a particular disease is. In an embodiment, a higher disease score may indicate a more severe disease. Life year score may include a numerical value indicating an estimated number of years that a user has left to live before succumbing to death. A "life value factor" as used in this disclosure, includes a numerical measurement indicating how similar traits may be between a user and cluster data entries contained within a particular cluster. Traits may include ethical and/or moral values of importance that a user may choose to encompass as part of their lifestyle. Traits may include for example authenticity, compassion, community, curiosity, friendship, generosity, honesty, kindness, knowledge, leadership, love, responsibility, security, self-respect, spirituality, stability, and/or wisdom. In an embodiment, a user may indicate the top 3-5 traits that are more important to a user.

With continued reference to FIG. 1, k-means clustering module 108 selects a classified data entry cluster 140 as a function of the degree of similarity index value. In an embodiment, k-means clustering module 108 may select a classified data entry cluster 140 with the smallest degree of similarity index value indicating a high degree of similarity between a user vibrancy datum 120 and a particular data entry cluster. In an embodiment, k-means clustering module 108 may not select a classified data entry cluster 140 with the largest degree of similarity index value indicating a low degree of similarity between a user vibrancy datum 120 and a particular data entry cluster.

With continued reference to FIG. 1, system 100 includes a k-nearest neighbors module 144 operating on at least a computing device. K-nearest neighbors module 144 may include any hardware and/or software module. K-nearest neighbors module 144 is designed and configured to receive from the K-means clustering module 108 the selected classified data entry cluster 140 and the at least a therapeutic constitutional inquiry 112; generate a k-nearest neighbors algorithm utilizing the selected classified data entry cluster 140 and the at least a therapeutic constitutional inquiry 112; identify a therapeutic dataset contained within the selected classified data entry cluster 140 wherein the selected classified data entry includes the at least a therapeutic constitutional inquiry 112 and a therapeutic remedy; generate a therapeutic remedy instruction set 156 as a function of identifying the therapeutic dataset; and display the therapeutic remedy instruction set 156 on a graphical user interface 116 located on the at least a computing device.

With continued reference to FIG. 1, k-nearest neighbors module 144 is configured to receive from k-means clustering module 108 the selected classified data entry cluster 140 and the at least a therapeutic constitutional inquiry 112. K-nearest neighbors module 144 may receive from k-means clustering module 108 selected classified data entry cluster 140 and the at least a therapeutic constitutional inquiry 112 utilizing any network topography as described herein. Selected classified data entry cluster 140 may be utilized by k-nearest neighbors module 144 as training data to generate a k-nearest neighbors algorithm 152 as described in more detail below. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a computing device and/or k-nearest neighbors module 144 may correlate any input data as described in this disclosure to any output data as described in this disclosure.

With continued reference to FIG. 1, k-nearest neighbors module 144 generates a k-nearest neighbors algorithm 152 utilizing the selected classified data entry cluster 140 and the at least a therapeutic constitutional inquiry 112. "K-nearest neighbors algorithm" as used in this disclosure, includes a lazy-learning method that utilizes feature similarity to analyze how closely out-of-sample-features resemble training data to locate possible optimal vector outputs, classify possible optimal vector outputs, calculate an optimal vector output and generate an optimal vector output. Optimal vector outputs may include vector outputs that may generate a desired outcome that satisfies a k-nearest neighbors algorithm. Calculating an optimal vector output utilizing a k-nearest neighbors algorithm 152 may include specifying a K-value, selecting k entries in a database which are closest to the known sample, determining the most common classifier of the entries in the database, and classifying the known sample. A lazy-learning process and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, generating k-nearest neighbors algorithm 152 includes generating a first vector output containing a data entry cluster, generating a second vector output containing at least a therapeutic constitutional inquiry 112 and calculate the distance between the first vector output and the second vector output using Euclidean distance measurement. A first vector output is n n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance be advantageous where each vector represents a weighing of priorities, and/or is to be compared to such a weighing of priorities. Priorities may be generated based on user input, where a user may prefer a particular attribute.

With continued reference to FIG. 1, generating k-nearest neighbors module 144 generates an optimal vector output as a function of the distance between the first vector output containing a data entry cluster and the second vector output containing the at least a therapeutic constitutional inquiry 112. K-nearest neighbors module 144 identifies a therapeutic dataset utilizing the optimal vector output.

With continued reference to FIG. 1, k-nearest neighbors module 144 identifies at least a therapeutic dataset contained within the selected classified data entry cluster 140. A "therapeutic dataset" as used in this disclosure, includes the at least a therapeutic constitutional inquiry 112 and a correlated therapeutic remedy. A therapeutic constitutional inquiry may be correlated to a therapeutic remedy by a shared trait whereby a therapeutic remedy may be utilized as a form of treatment for a therapeutic constitutional inquiry. For example, a therapeutic constitutional inquiry such as a headache may be correlated to a therapeutic remedy such as aspirin. In yet another non-limiting example, a therapeutic constitutional inquiry such as heartburn may be correlated to a therapeutic remedy such as an antacid. A "therapeutic remedy" as used in this disclosure, includes any data that identifies a process that improves a current, incipient, or probable future medical condition affecting a person contained within a therapeutic constitutional inquiry 112. Prescriptive processes may include, without limitation, dietary or nutritional recommendations based on data including nutritional content, digestibility, or the like. Prescriptive processes may include one or more medical procedures. Prescriptive processes may include one or more physical, psychological, or other therapies. Prescriptive processes may include one or more medications, supplements, homeopathic remedies, herbs, therapies, and the like. For instance and without limitation, a therapeutic remedy may include a combination of supplements that may be utilized to treat a user with a medical condition such as Lyme Disease. In yet another non-limiting example, a therapeutic remedy may include a prescription medication that may be utilized to treat a user with a medication condition such as cystic fibrosis.

With continued reference to FIG. 1, k-nearest neighbors module 144 is configured to generate a therapeutic remedy instruction set 156 as a function of identifying a therapeutic dataset. A 'therapeutic remedy instruction set 156" as used in this disclosure, includes data identifying one or more therapeutic remedies selected from one or more therapeutic datasets that have been utilized to treat the same therapeutic constitutional inquiry 112. For instance and without limitation, k-nearest neighbors module 144 may identify three therapeutic datasets by generating k-nearest neighbors algorithm 152 utilizing the selected classified data entry cluster 140. In such an instance, three therapeutic datasets may include a first therapeutic dataset containing a therapeutic constitutional inquiry 112 such as type two diabetes mellitus and a first therapeutic remedy such as metformin; a second therapeutic dataset containing the same therapeutic constitutional inquiry 112 of type two diabetes mellitus and a second therapeutic remedy such as cinnamon bark capsules and chromium picolinate; and a third therapeutic dataset containing the same therapeutic constitutional inquiry 112 of type two diabetes mellitus and a third therapeutic remedy such as ginseng.

With continued reference to FIG. 1, k-nearest neighbors module 144 is configured to display a therapeutic remedy instruction set 156 on a graphical user interface 116 located on at least a computing device. Graphical user interface 116 may include any of the graphical user interface 116 as described above.

With continued reference to FIG. 1, system 100 includes a wearable device 164 for calculating a therapeutic remedy result. A "device," as used in this disclosure, is a computing device, including but not limited to a mobile device such as a smartphone, tablet, laptop, desktop, and the like. Wearable device 164 includes a display 168. A "display," as used in this disclosure, is an interface that allows a user to interface with computing device 104 through graphical icons, audio indicators, command labels, text navigation and the like. Display 168 may include slides or other user commands that may allow a user to select one or more characters. Display 168 may include free form textual entries, where a user may type in responses and/or messages. Display 168 may include data input fields such as text entry windows, drop-down lists, buttons, checkboxes, radio buttons, sliders, links, or any other data input interface that may capture user interaction as may occur to persons skilled in the art upon reviewing the entirety of this disclosure. Display 168 may be provided, without limitation, using a web browser, a native application, a mobile application or the like.

With continued reference to FIG. 1, wearable device 164 includes a sensor 172. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a weight scale. A sensor may include a temperature sensor. A sensor may include any sensor that may be included in wearable device 164, including for example, a mobile device and/or wearable device, including without limitation a motion sensor such as an inertial measurement unit (IMU), one or more accelerometers, one or more gyroscopes, one or more magnetometers, or the like. A wearable and/or mobile device sensor may capture step, gait, and/or other mobility data, as well as data describing activity levels and/or physical fitness. A wearable and/or mobile device sensor may detect heart rate or the like. A sensor may detect any hematological parameter including blood oxygen level, pulse rate, heart rate, pulse rhythm, blood glucose and/or blood pressure.

With continued reference to FIG. 1, wearable device 164, includes a computing device 104 in communication with display 168 and sensor 172. Computing device 104 includes any computing device as described herein. Computing device 104 is configured to record a user vibrancy datum 120; for instance, and without limitation, computing device 104 the user vibrancy datum using sensor 172. A user vibrancy datum 120, includes any component of a vibrancy record, as described above in more detail. For instance and without limitation, a user vibrancy datum 120 may contain a record of one or more meals that a user ordered out and consumed over the previous week. In yet another non-limiting example, a user vibrancy datum 120 may contain a measurement obtained by sensor 172 that contains a user's blood pressure upon waking. Information pertaining to a user vibrancy datum 120 may be recorded and stored within vibrancy database 124. Computing device 104 is configured to record a user vibrancy datum 120 at a timed interval. A "timed interval," as used in this disclosure, is any intervening period of time. A timed interval may include a specified period of time. For instance and without limitation, computing device 104 may be configured to measure a user's blood glucose level at a set period of time, such as every two hours. In yet another non-limiting example, computing device 104 may be configured to measure a user's blood pressure once daily. In an embodiment, a user may specify a timed interval that the user would prefer to have the user's vibrancy datum recorded at. For example, a user may specify that the user would like the user's heart rate to be measured at 9 pm every evening.

With continued reference to FIG. 1, computing device 104 is configured to retrieve a user vibrancy record and identify a therapeutic indication contained within the user vibrancy record. A "therapeutic indication," as used in this disclosure, is documentation specifying one or more previous, current, and/or future probable medical conditions, diagnoses, syndromes, medical evidence, and the like that warrant the use of a therapeutic remedy. For instance and without limitation, a therapeutic indication may identify a user who has pre-diabetes. In yet another non-limiting example, a therapeutic indication may identify a user who has a future probable chance of developing Alzheimer's disease, because of the presence of an Apolipoprotein E4 gene. Information pertaining to a therapeutic indication may be stored within user database 160. Computing device 104 selects a user vibrancy datum to record as a function of a therapeutic indication. For instance and without limitation, a therapeutic indication that identifies a user as having atrial fibrillation may require a user to have the user's heart rate monitored and measured. In yet another non-limiting example, a therapeutic indication that identifies a user as having low serotonin may require a user to have the user's sleep patterns monitored and tracked. Computing device 104 is configured to identify an environmental indicator relating to a user vibrancy datum, and record the environmental indicator relating to the user vibrancy datum. An "environmental indicator," as used in this disclosure, is an identifier of any surroundings and/or conditions in which a user vibrancy datum is recorded. An environmental indicator may include a geolocation, such as the identification of the geographical location of a user and/or wearable device 164. A geolocation may include a global positioning system (GPS) of a user, including for example, the GPS location of wearable device 164. A geolocation may include a description of the latitude and longitude of a position where a user is currently located and/or a position where a user may be located in the future. An environmental indicator may include a description of a user's surroundings, such as if the user were outside in open air, or if the user was inside the user's house by the user's kitchen. An environmental indicator may include a description of a task a user was completing and/or in the process of completing while a user vibrancy datum 120 was recorded. For instance and without limitation, an environmental indicator may specify that a user had just completed a 20 minute brisk walk before the user's blood sugar was recorded. In yet another non-limiting example, an environmental indicator may specify that was user was staying at a hotel in Mexico City, Mexico, when the user experienced an epileptic seizure. Information pertaining to an environmental indicator may be stored within user database 160.

With continued reference to FIG. 1, computing device 104 identifies a therapeutic remedy instruction set 156 using a user vibrancy datum 120, where the therapeutic remedy instruction set 156 includes a therapeutic remedy. Therapeutic remedy includes any of the therapeutic remedies as described above. Information pertaining to a therapeutic remedy may be stored within user database 160. In an embodiment, a user vibrancy datum 120 may contain one or more identifiers pertaining to a user, which may be utilized to identify a therapeutic remedy instruction set. An identifier may include any information pertaining to a user, including the user's name, address, birthday, social security number, fingerprints, photograph, and the like. An identifier may be used to locate a therapeutic remedy instruction set 156 contained within user database 160.

With continued reference to FIG. 1, computing device 104 is configured to calculate a therapeutic remedy result that associates a user vibrancy datum 120 with a therapy response curve. A "therapeutic remedy result," as used in this disclosure, is an indication as to a user's progress and/or compliance with a therapeutic remedy. For instance and without limitation, a therapeutic remedy result may indicate that a user has elevated blood glucose, despite being compliant with taking a blood glucose lowering supplement. In yet another non-limiting example, a therapeutic remedy result may indicate that a user has lost ten pounds since initiating a yoga practice twice each week. A "therapy response curve," as used in this disclosure, is a data set that represents a user's progress over time with a therapeutic remedy. In an embodiment, a therapy response curve may be depicted as a graphical and/or pictorial representation of a user's progress over time with a therapeutic remedy. For example, a therapy response curve may illustrate how a user's blood pressure readings have fluctuated since the user started a nightly meditation practice. In yet another non-limiting example, a therapy response curve may illustrate that a user's weight has steadily declined since starting a ketogenic diet.

With continued reference to FIG. 1, computing device 104 may be configured to generate a response label as a function of a therapy response curve. A "response label," as used in this disclosure, is any feedback generated using a therapy response curve. A response label may be displayed to a user, using display 168. In an embodiment, a response label may contain any remarks, words of encouragement, suggestion, and/or feedback in relation to a therapy response curve. For instance and without limitation, a response label may encourage a user to continue walking for thirty minutes every day, when a therapy response curve demonstrates that a user has lost seven pounds since scheduling a walk for three days each week for the previous six months. In an embodiment, a response label may contain character, numerical, and/or textual responses. Computing device 104 is configured to display an alert, when a response label comes below a threshold parameter. A "threshold parameter," as used in this disclosure, is a point at which a user may be danger and/or require additional assistance and trigger an alert. A threshold parameter may indicate a point at which a user vibrancy datum 120 indicates a user is in distress. For example, a threshold parameter may be triggered when a user's blood pressure remains elevated over the course of three or more readings and requires medical attention and intervention. A threshold parameter may indicate a point at which a user vibrancy datum 120 indicates an abnormal pattern of behavior and/or a dramatic change in a series of readings of user vibrancy datums 120. For instance and without limitation, a threshold parameter may indicate that a user who had a series of previously recorded heart rate measurements that were within normal limits, suddenly has one or more abnormal measurements. In an embodiment, a threshold parameter may be selected and/or preset by a user and/or a user's medical professional such as a doctor, nurse, and the like. For example, a user's doctor may indicate that an alert should be triggered to a user when the user's blood glucose falls below 70 milligrams per deciliter.

With continued reference to FIG. 1, computing device 104 is configured to record a first user vibrancy datum 120 relating to an event. An "event," as used in this disclosure, is the onset of a situation manifested by symptoms of specified severity. For instance and without limitation, an event may include a medical emergency such as a heart attack characterized by chest pain, tightness, shortness of breath, coughing, wheezing, and feeling of being sick. In yet another non-limiting example, an event may include an adverse drug reaction, such as a prescription medication that causes skin rash, hives, itching, fever, wheezing and the like. In yet another non-limiting example, an event may include a hypoglycemic episode, characterized by excessive sweating, irritability, confusion, elevated heartbeat, hunger, thirst, and the like. Computing device 104 establishes a user response as a function of a first user vibrancy datum. A "user response," as used in this disclosure, is a user's physiological response to an event. A user response may include any inputs generated by a user about the event, such as a user who reports experiencing a seizure. In yet another non-limiting example, a user response may include one or more user vibrancy datums 120 that were recorded and collected during an event. For example, a user response may include a measurement of a user's blood pressure during a hypertensive crisis. A user response may include information relating to where a user was located when an event occurred, what type of day the event occurred at, what the user was doing when the event occurred, any personal and/or business related events that occurred leading up to the event, what type of environment the user was located within, and the like. Computing device 104 identifies a user response as a function of a second user vibrancy datum and displays a message relating to the event. For instance and without limitation, computing device 104 may record a user's blood glucose level during a hypoglycemic episode. Computing device 104 establishes a user response, which indicates that the user experienced a low blood glucose reading of 41 milligrams per deciliter. In such an instance, computing device 104 may identify a user response of a second hypoglycemic episode when the user has a subsequent blood glucose reading of 55 milligrams per deciliter and display a message to the user informing the user that the user is experiencing a hypoglycemic episode. In an embodiment, an alert may include one or more auditory alerts, to seek the attention of a user's family member or friend who may be close by and may be able to help a user. In an embodiment, an alert may display one or more suggestions and/or recommendations for a user to seek medical attention.

With continued reference to FIG. 1, computing device 104 is configured to locate information relating to a user's program. A "user's program," as used in this disclosure, is one or more elements of scheduling information relating to a user's day to day calendar. A user's program may include any work, school, and/or personal commitments that the user may be engaged in on a particular day. For example, a user's program may indicate that a user has a standing appointment with the user's dermatologist on the third Wednesday of every month at 3 pm for an hour long appointment. In yet another non-limiting example, a user's program may specify that a user cycles three morning each week at 6 am. Computing device 104 identifies an opening contained within a user's program and creates an entry relating to a therapeutic remedy. An "opening," as used in this disclosure, is a time slot in a user's schedule, when a user has free time, and does not have anything else scheduled. For example, computing device 104 may identify an opening contained within a user's program on Tuesday and Thursday evenings at 8 pm, and create an entry scheduling a meditation sequence for a user to practice, relating to the user's therapeutic remedy to develop a meditation practice. In yet another non-limiting example, computing device 104 may identify an opening contained within a user's program every morning at 7 am, and create an entry scheduling a reminder for a user to take a blood pressure medication. Computing device 104 is configured to record a user vibrancy datum during an entry. For example, computing device 104 may measure a user's heart rate and blood pressure while the user engages in a meditation sequence. In yet another non-limiting example, computing device 104 may measure a user's blood glucose level after the user engaged in an hour of vigorous exercise. Computing device 104 generates a completion index as a function of a user vibrancy datum 120. A "completion index," as used in this disclosure, is an analysis as to what portion of a therapeutic remedy was completed during a specified time. For example, a completion index may specify that a user completed ten minutes of a 30 minute guided meditation sequence. In yet another non-limiting example, a completion index may specify that a user completed an entire sixty minute yoga class on two separate days. Computing device 104 displays a response relating to a completion index. A response may contain a suggestion, words of encouragement, critique, and the like relating to a completion index. For example, a user who completes ten minutes of cardiovascular exercise may receive a response containing a suggestion for the user to try twelve minutes of cardiovascular exercise next time. In yet another non-limiting example, a user who completed a meditation sequence for six nights in a row may receive a response encouraging the user to continue to practice the meditation sequence.

With continued reference to FIG. 1, computing device 104 calculates a therapeutic remedy using therapy training data. "Therapy training data," as used in this disclosure, is training data that contains a plurality of data entries containing user vibrancy datums and therapeutic remedy instruction sets, correlated to therapeutic remedy results. Therapy training data is used to train a therapy machine-learning process. A "therapy machine-learning process," as used in this disclosure, is a machine-learning process that uses a user vibrancy datum and a therapeutic remedy as an input, and outputs a therapy response remedy result. A therapy machine-learning process may be implemented as any machine-learning process as described herein. A therapy machine-learning process is utilized to generate a therapeutic remedy result.

With continued reference to FIG. 1, computing device 104 is configured to insert a user vibrancy datum 120 and a therapeutic remedy instruction set into a user vibrancy record. Inserting a user vibrancy datum 120 and a therapeutic remedy instruction set may include incorporating a user vibrancy datum 120 and a therapeutic remedy instruction set into a user vibrancy record. Computing device 104 updates a user vibrancy record as a function of inserting a user vibrancy datum and a therapeutic remedy instruction set.

Figure 2:
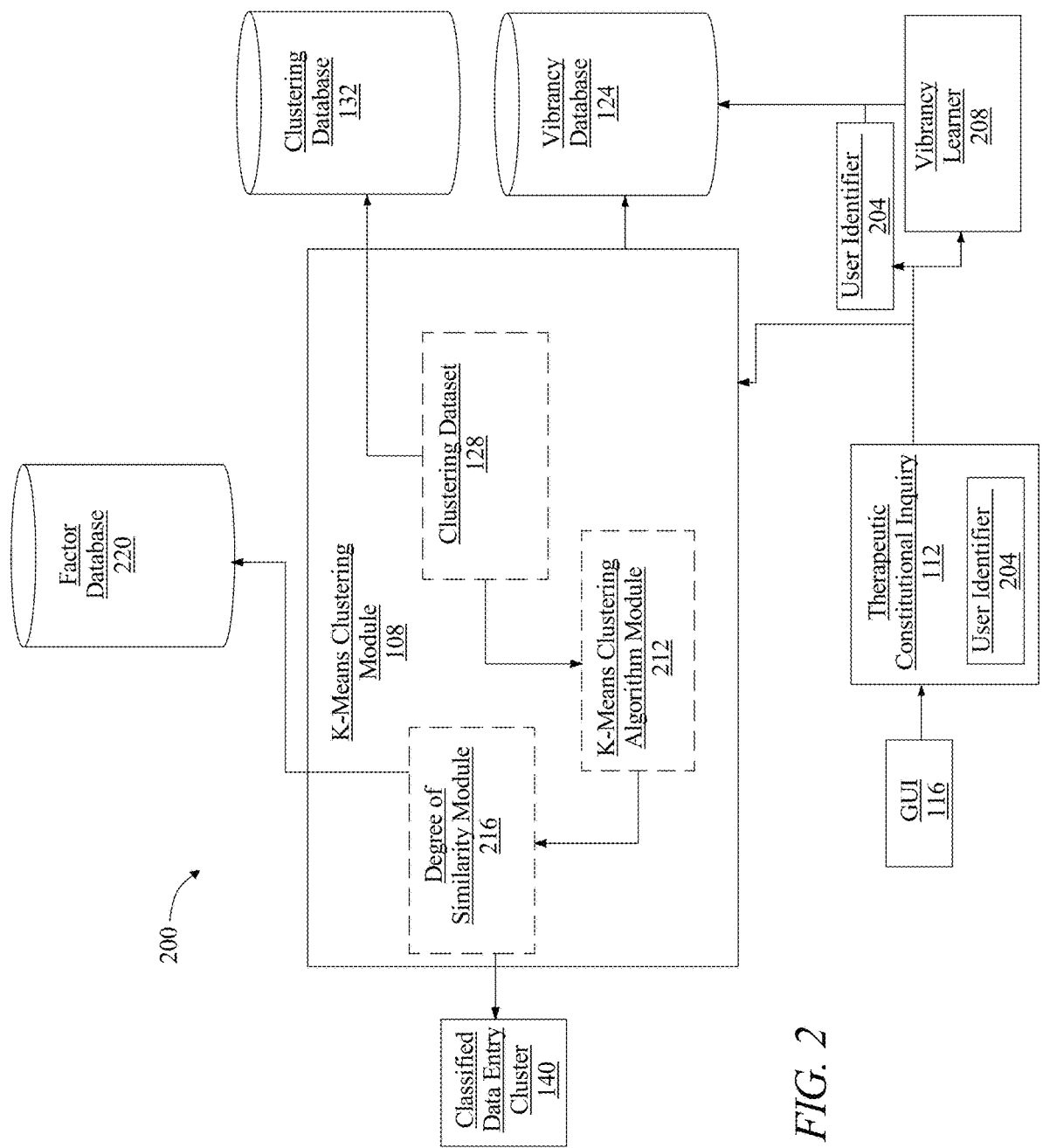
FIG. 2 is a block diagram illustrating an exemplary embodiment of a k-means clustering algorithm.

Referring now to FIG. 2, an exemplary embodiment 200 of k-means clustering module 108 is illustrated. K-means clustering module 108 receives at least a therapeutic constitutional inquiry 112 input from a graphical user interface 116 by a therapeutic professional. Therapeutic constitutional inquiry 112 input includes any of the therapeutic constitutional inputs as described above in reference to FIG. 1. For instance and without limitation, therapeutic constitutional inquiry 112 input may include a current diagnosed medical condition that a user may have been diagnosed with such as Alzheimer's disease. In yet another non-limiting example, therapeutic constitutional input may include a current diagnosis such as methane positive small intestinal bacterial overgrowth. Therapeutic constitutional inquiry 112 includes a user identifier 204. User identifier 204 may include any of the user identifiers as described above in reference to FIG. 1. User identifier may be utilized by k-means clustering module 108 to locate a user vibrancy record within vibrancy database 124.

With continued reference to FIG. 2, vibrancy database 124 may include any database structure as described above in reference to FIG. 1. Vibrancy database 124 may include data entries regarding a user's medical profile as described above in more detail in reference to FIG. 1. Vibrancy database 124 may include for example, medical record data including immunization records, lab results, clinical notes, and the like as described above in more detail in reference to FIG. 1. K-means clustering module 108 locates a user vibrancy record containing a plurality of user vibrancy datum 120 stored in a vibrancy database 124 as a function of the user identifier. K-means clustering module 108 may verify a user vibrancy record by comparing the user identifier received with a therapeutic constitutional inquiry 112 to a user identifier stored in a user vibrancy record. K-means clustering module 108 may verify a user identifier when the user identifier received with a therapeutic constitutional inquiry 112 matches a user identifier stored in a user vibrancy record. K-means clustering module 108 may not verify a user identifier when the user identifier received with a therapeutic constitutional inquiry 112 does not match a user identifier stored in a user vibrancy record. In an embodiment, k-means clustering module 108 may verify a user identifier such as using cryptographic means including comparing a hash, using a public/private key pair, and the like.

With continued reference to FIG. 2, k-means clustering module 108 may include a vibrancy learner 208 that may select at least a user vibrancy datum 120 as a function of the at least a therapeutic constitutional inquiry 112. Vibrancy learner 208 may include any hardware and/or software module. Vibrancy learner 208 may be configured to select a user vibrancy datum 120 related to a therapeutic constitutional inquiry 112 using machine-learning processes. For instance and without limitation, vibrancy learner 208 may be configured to select a user vibrancy datum 120 that includes a lab test showing a genetic mutation to the LCT gene responsible for the production of the enzyme lactase to a therapeutic constitutional inquiry 112 that includes a medical condition of lactose intolerance. In yet another non-limiting example, vibrancy learner 208 may be configured to select a user vibrancy datum 120 that includes a medical progress notes that show progressive worsening of a user's symptoms over a six month span related to a therapeutic constitutional inquiry 112 containing a diagnosis of multiple sclerosis. A machine-learning process is a process that automatedly uses a body of data known as "training data" and/or a "training set" to generate an algorithm that will be performed by a computing device and/or module to produce outputs given data provided as inputs; this is in contrast to a non-machine-learning software program where the commands to be executed are determined in advance by a user and written in a programming language.

Still referring to FIG. 2, vibrancy learner 208 may be designed and configured to select at least a user vibrancy datum 120 by creating a machine-learning model relating therapeutic constitutional inquiries to user vibrancy datum 120 using a training set and selecting a user vibrancy datum 120 using the machine-learning model; at least a machine-learning model may include one or more models that determine a mathematical relationship between therapeutic constitutional inquiries and user vibrancy datum 120. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 2, machine-learning algorithm used to generate machine-learning model may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors' algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

With continued reference to FIG. 2, K-means clustering module 108 receives a clustering dataset 128. K-means clustering module 108 may receive clustering dataset 128 from clustering database 132. Clustering database 132 may include any data structure suitable for use as vibrancy database 124. Clustering database 132 may include clustering dataset 128 that include a plurality of unclassified cluster data entries. Clustering dataset 128 may be obtained from medical records and charts as well as from expert inputs as described above in reference to FIG. 1. Clustering dataset 128 may be organized within clustering dataset 128 according to common shared characteristics. For instance and without limitation, clustering dataset 128 may be organized according to shared traits of cluster data entries contained within clustering dataset 128 such as clustering dataset 128 that contain cluster data entries from users who are between the ages of 45-55 years old or cluster data entries from users who have all been diagnosed with Lupus. Organization of clustering dataset 128 is described below in more detail.

With continued reference to FIG. 2, k-means clustering module 108 may include k-means clustering algorithm 136 module 212. K-means clustering algorithm 136 module 212 may include any hardware and/or software module. K-means clustering algorithm 136 module 212 generates k-means clustering algorithm 136 using the clustering dataset 128 received from clustering database 132. K-means clustering algorithm 136 module 212 receives clustering dataset 128 as input and outputs a definite number of classified data entry cluster 140 that each contain cluster data entries. K-means clustering algorithm 136 module 212 may determine k-value that will set a fixed number of classified data entry cluster 140 as outputs utilizing any of the methods as described above in reference to FIG. 1. In an embodiment, k-value may be selected based generating k-means clustering algorithm 136 repeatedly until a k-value is averaged and selected. In yet another non-limiting example, a k-value may be selected based on a particular clustering dataset 128 that may be best suited for a particular k-value. K-means clustering algorithm 136 module receives as input unclassified clustering dataset 128. Unclassified clustering dataset 128 may include any of the unclassified clustering dataset 128 as described above in reference to FIG. 1. K-means clustering algorithm 136 module outputs classified data entry cluster 140. Data entry clusters may be classified by k-means clustering algorithm 136 module using predictive modeling that approximates a mapping function from input variables to discrete output variables. Classification may be performed utilizing classification algorithms that include for example decision trees, naïve bayes, artificial neural networks, boosting, kernel methods, and/or k-nearest neighbors algorithms. K-means clustering algorithm 136 module may generate a soft k-means clustering algorithm 136 wherein a "soft k-means clustering algorithm" as used in this disclosure includes a k-means clustering algorithm where a cluster data entry may be selected and/or assigned to multiple clusters of the definite number of classified data entry cluster 140. For instance and without limitation, k-means clustering algorithm 136 module may generate a soft k-means clustering algorithm 136 that has a k-value of seven and where a particular cluster data entry may be selected and assigned to three of the seven classified data entry cluster 140. K-means clustering algorithm module may generate a hard k-means clustering algorithm 136 wherein a "hard k-means clustering algorithm" as used in this disclosure includes a k-means clustering algorithm where a cluster data entry may be selected to be assigned to one cluster of the definite number of classified data entry cluster. For instance and without limitation, k-means clustering algorithm 136 module may generate a hard k-means clustering algorithm 136 that has a k-value of seven and where a particular cluster data entry may be selected and assigned to one of the seven classified data entry cluster 140. K-means clustering algorithm 136 module may select a hard k-means algorithm and/or a soft k-means algorithm based on expert input as described in more detail below. In an embodiment, k-means clustering algorithm 136 module may select a hard k-means algorithm and/or a soft k-means algorithm based on learned associations between clustering dataset 128 and classified data entry outputs such as by learned associations such as from vibrancy learner 208.

With continued reference to FIG. 2, k-means clustering module 108 may include degree of similarity module 216. Degree of similarity module 216 may include any hardware and/or software module. Degree of similarity module 216 may calculate a degree of similarity index value that contains a distance measurement between a data entry cluster and a user vibrancy datum 120. Degree of similarity index value may include any of the degree of similarity index values as described above in reference to FIG. 1. Degree of similarity index value may include a background factor multiplied by an age factor and a vibrancy factor and divided by a life value factor. Factors utilized to calculate degree of similarity index value may be included in factor database 220. Factor database 220 may include any data structure suitable for use as vibrancy database 124 as described in more detail below.

With continued reference to FIG. 2, degree of similarity module may evaluate degree of similarity index value for a particular classified data entry cluster 140 and select a classified data entry cluster 140 as a function of the degree of similarity index value. In an embodiment degree of similarity module may select a classified data entry cluster 140 that is the most similar to user vibrancy datum 120. In an embodiment, classified data entry cluster 140 that contains the smallest numerical score for the similarity index value may indicate the most similar classified data entry cluster 140 to a selected user vibrancy datum 120. Similarity index value module may be configured to calculate and evaluate similarity index values.

Figure 3:
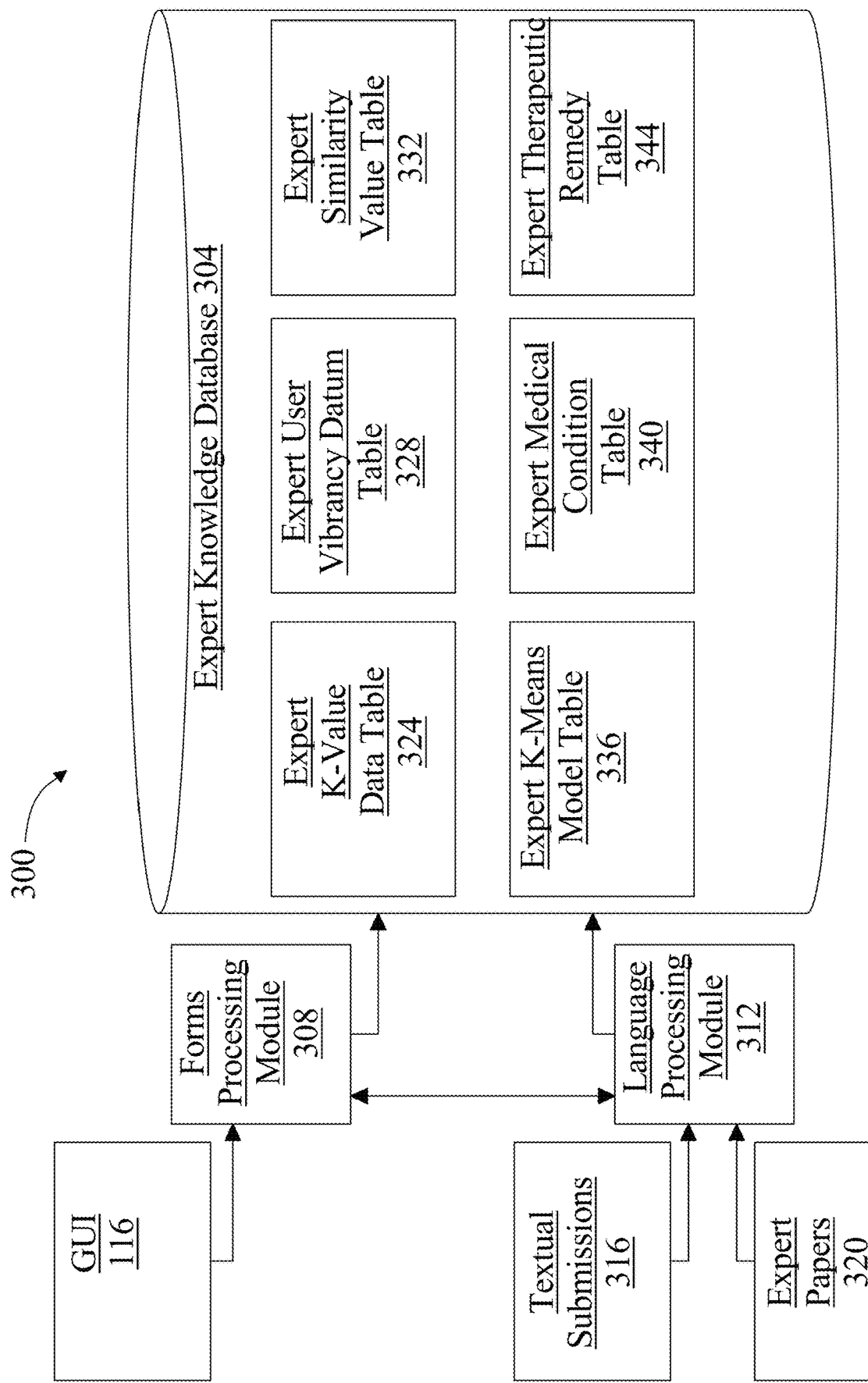
FIG. 3 is a block diagram of an exemplary embodiment of an expert knowledge database.

Referring now to FIG. 3, an exemplary embodiment 300 of expert knowledge database 304 is illustrate. Expert knowledge database may include any data structure and/or data store suitable for use as vibrancy database 124 as described above. One or more database tables may be linked to one another by, for instance, common column values. For instance, a common column between two tables of expert knowledge database may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 3, expert knowledge database includes a forms processing module 308 that may sort data entered in a submission via graphical user interface 116 by, for instance, sorting data from entries in the graphical user interface 116 to related categories of data; for instance, data entered in an entry relating in the graphical user interface 116 to a medical condition may be sorted into variables and/or data structures for storage of medical conditions, while data entered in an entry relating to a category of vibrancy datum and/or an element thereof may be sorted into variables and/or data structures for the storage of, respectively, categories of vibrancy datums. Where data is chosen by an expert from pre-selected entries such as drop-down lists, data may be stored directly; where data is entered in textual form, language processing module 312 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 312 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 316, such as accomplished by filling out a paper or PDF form and/or submitting narrative information, may likewise be processed using language processing module 312. Data may be extracted from expert papers 320, which may include without limitation publications in medical and/or scientific journals, by language processing module 312 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 3, one or more tables contained within expert knowledge database may include expert k-value data table 324; expert k-value data table 324 may include one or more data entries describing expert input regarding k-values for clustering dataset 128 and/or therapeutic constitutional inquiries. One or more tables contained within expert knowledge database may include expert user vibrancy datum 120 table 328; expert user vibrancy datum 120 table 328 may include one or more data entries describing expert input regarding therapeutic constitutional inquiries and related user vibrancy datum 120. One or more tables contained within expert knowledge database may include expert similarity value table 332; expert similarity value table 332 may include one or more data entries describing expert similarity values and/or calculations. One or more tables contained within expert knowledge database may include expert k-means model table 336; expert k-means model table 336 may include one or more data entries describing expert input regarding calculations of k-means model. One or more tables contained within expert knowledge database may include expert medical condition table 340; expert medical condition table 340 may include one or more data entries describing expert input regarding medical conditions. One or more tables contained within expert knowledge database may include expert therapeutic remedy table 344; expert therapeutic remedy table 344 may include one or more data entries describing expert therapeutic remedies.

Figure 4:
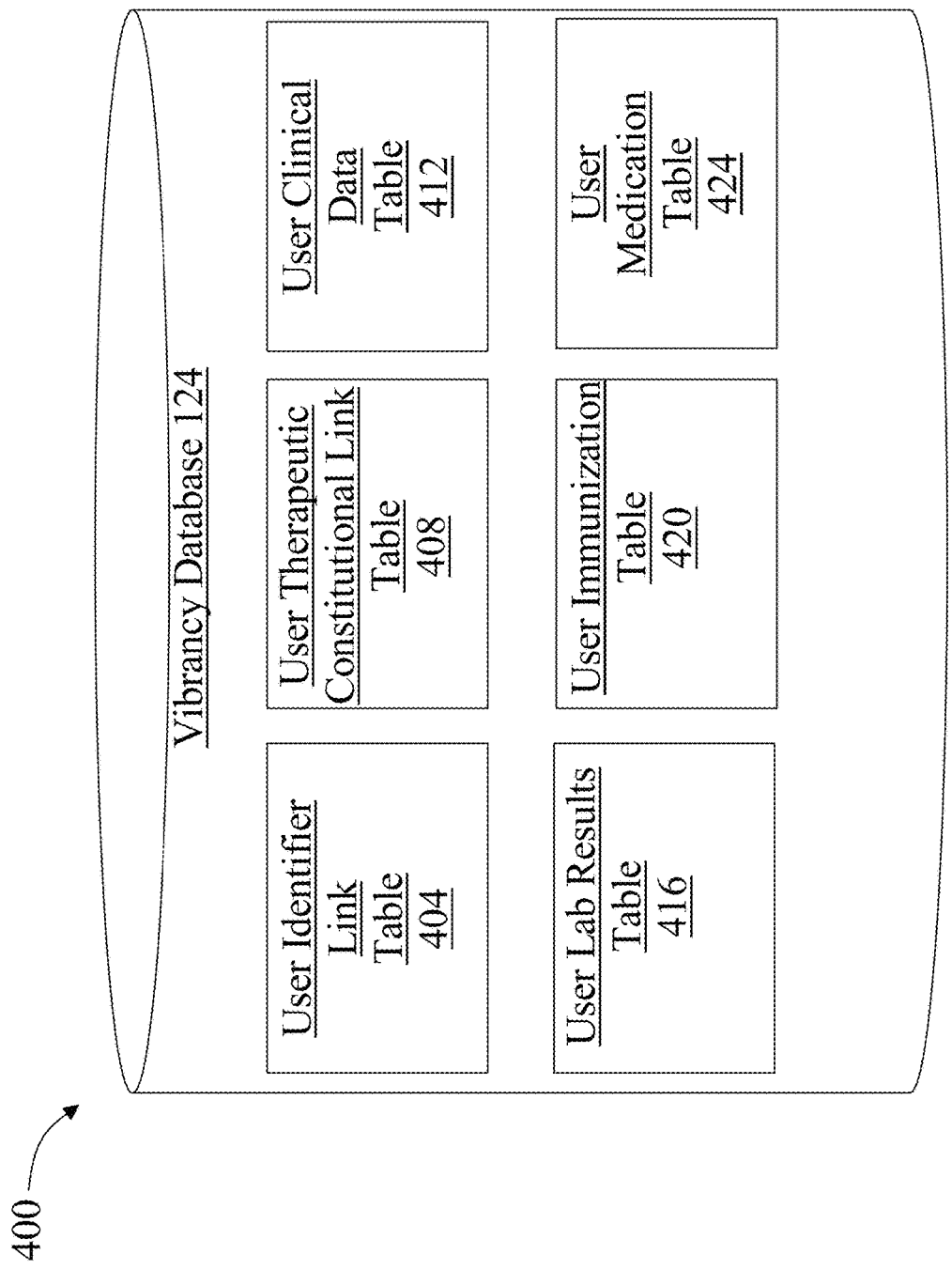
FIG. 4 is a block diagram illustrating an exemplary embodiment of a vibrancy database.

Referring now to FIG. 4, an exemplary embodiment of vibrancy database 124 is illustrated. Vibrancy database 124 may include any data structure as described above in reference to FIG. 1. One or more tables contained within vibrancy database 124 may include user identifier link table 404; user identifier link table 404 may include information describing a user identifier. For instance and without limitation, user identifier link table may include data entries containing a list of users and associated user identifiers that may be utilized to verify a user identifier as compared to a user identifier contained within a therapeutic constitutional inquiry 112. One or more tables contained within vibrancy database 124 may include user therapeutic constitutional link table 408; user therapeutic constitutional link table 408 may include one or more data entries containing a user therapeutic constitutional inquiry 112 linked to a user vibrancy datum 120. For instance and without limitation, user therapeutic constitutional link table 408 may include a therapeutic constitutional inquiry 112 such as type two diabetes mellitus linked to a user vibrancy datum 120 such as a fasting hemoglobin A1C. One or more tables contained within vibrancy database 124 may include user clinical data table 412; user clinical data table 412 may include one or more data entries containing user clinical data. For instance and without limitation, user clinical data table 412 may include one or more data entries describing the health status of a user over a specific period of time. One or more tables contained within vibrancy database 124 may include user lab results table 416; user lab results table 416 may include one or more data entries containing user lab results. For instance and without limitation, user lab results table 416 may include one or more user label results such as a blood sample analyzed as part of a chem-7 panel, or a hair sample analyzed for a particular genetic mutation. One or more tables contained within vibrancy database 124 may include user immunization table 420; user immunization table 420 may include one or more data entries describing the immunization records of a user. For instance and without limitation, user immunization table 420 may include data describing the date a user received a tetanus immunization, along with information describing the dose, location where administered, as well as the lot number and manufacturer of the tetanus immunization. One or more tables contained within vibrancy database 124 may include user medication table 424; user medication table 424 may include one or more data entries describing the medication history a user. For instance and without limitation, user medication table 424 may include data describing medications that a user consumed over a particular period of time. User medication table 424 may include information regarding both prescription medication and nonprescription medications including over the counter medications, supplements, herbals, nutraceuticals, homeopathic remedies, and the like.

Figure 5:
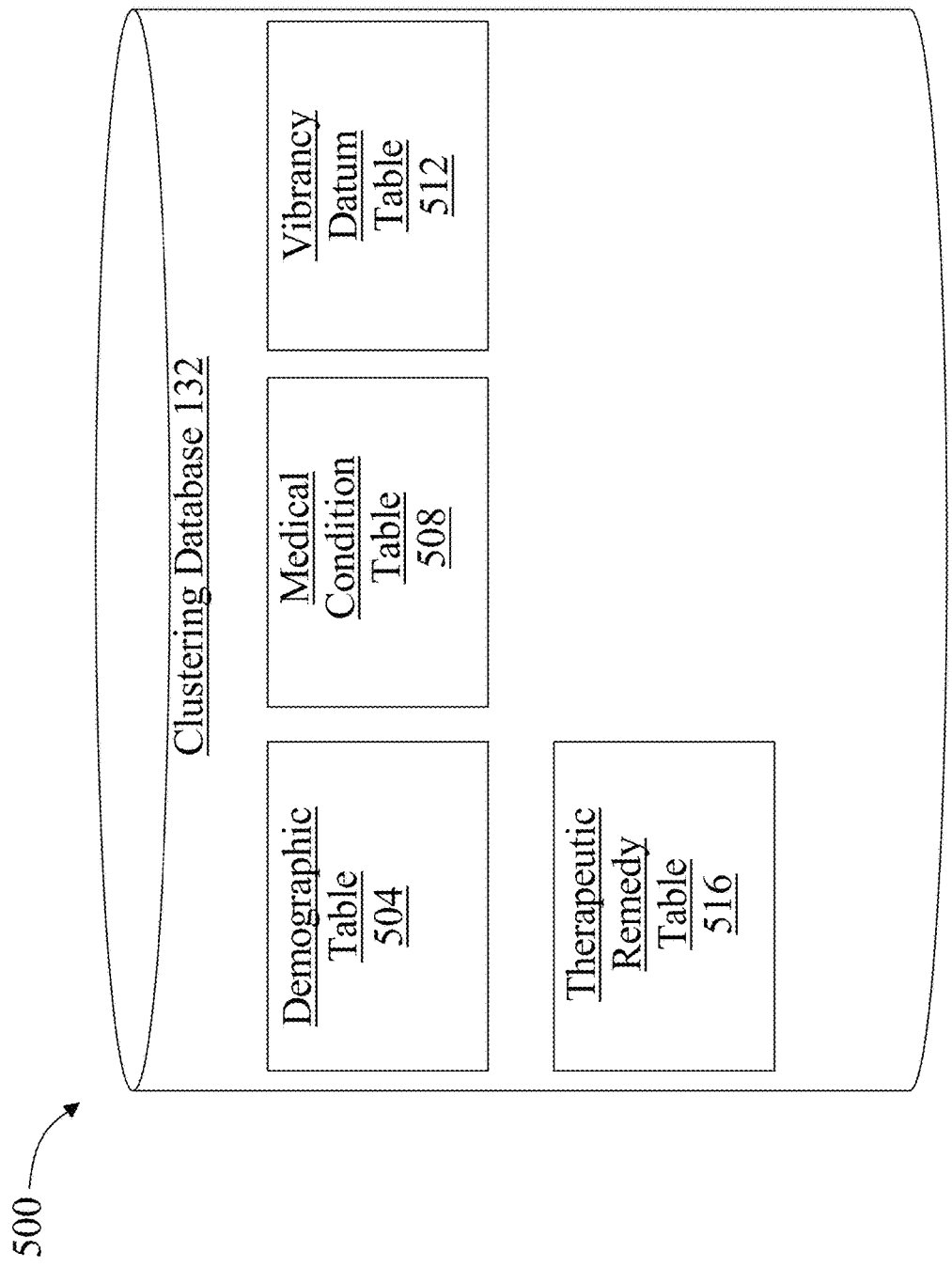
FIG. 5 is a block diagram illustrating an exemplary embodiment of a clustering database.

Referring now to FIG. 5, an exemplary embodiment of clustering database 132 is illustrated. Clustering database 132 may include any data structure suitable for use as vibrancy database 124. One or more tables contained within clustering database 132 may include demographic table 504; demographic table may include one or more clustering dataset 128 organized by demographics. For instance and without limitation, demographic table 504 may include one or more clustering dataset 128 organized by age, race, occupation, income, and the like. One or more tables contained within clustering database 132 may include medical condition table 508; medical condition table 508 may include one or more clustering dataset 128 organized by medical condition. For instance and without limitation, medical condition table 508 may include one or more clustering dataset 128 organized by medical condition such as lupus, multiple sclerosis, type one diabetes mellitus, hypothyroidism, and the like. One or more tables contained within clustering database 132 may include vibrancy datum table 512; vibrancy datum table 512 may include one or more clustering dataset 128 organized by vibrancy datum. For instance and without limitation, vibrancy datum table may include one or more clustering dataset 128 organized by lab result, tissue sample, clinical note, medication, and the like. One or more tables contained within clustering database 132 may include therapeutic remedy table 516; therapeutic remedy table 516 may include one or more clustering dataset 128 organized by therapeutic remedy. For instance and without limitation, therapeutic remedy table 516 may include one or more clustering dataset 128 organized by a particular therapeutic remedy including for example medication name, medication dose, supplement name, meditation sequence, prayer sequence, and the like.

Figure 6:
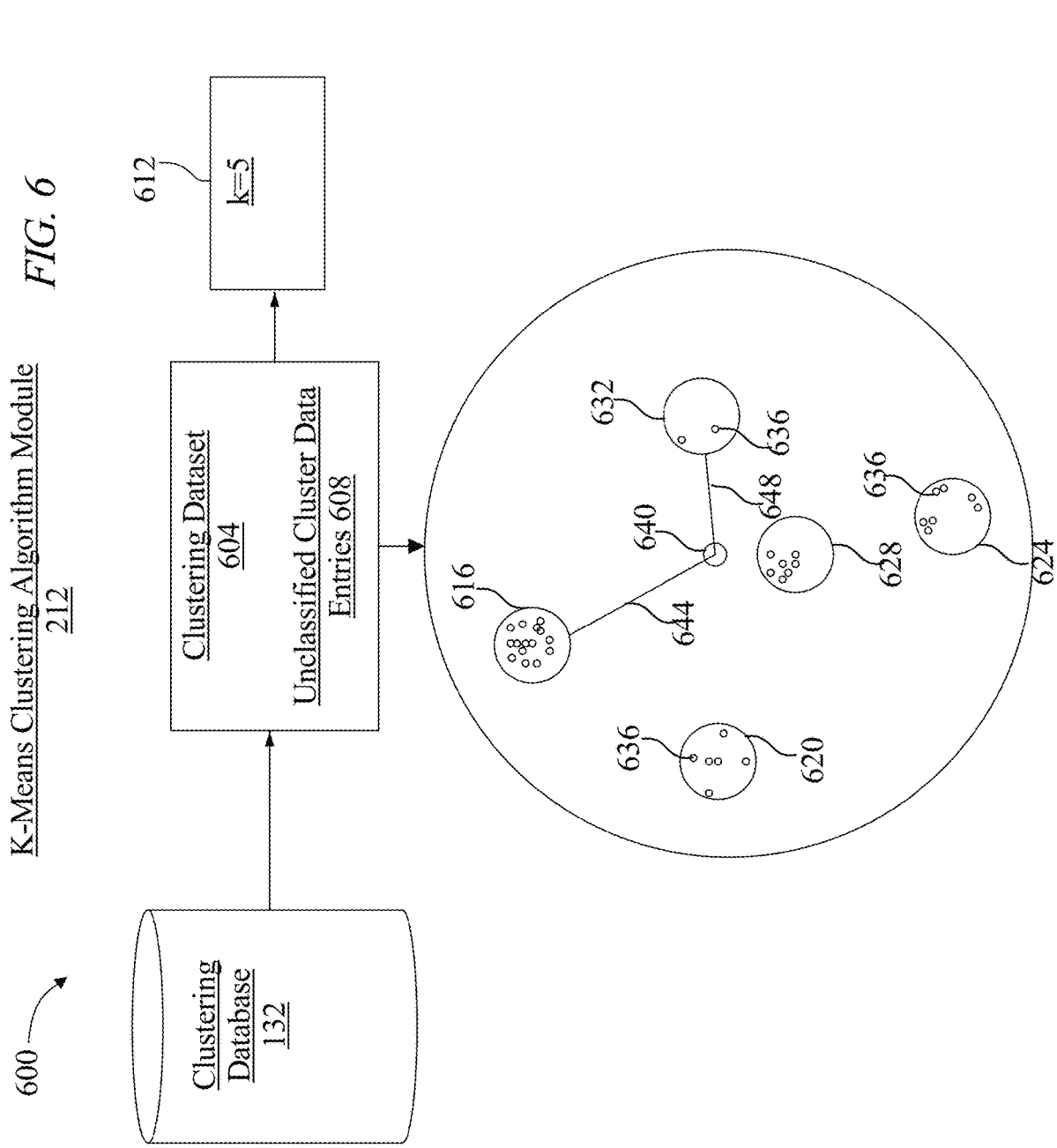
FIG. 6 is a diagrammatic representation of a k-means clustering algorithm module.

Referring now to FIG. 6, an exemplary embodiment 600 of k-means clustering algorithm 136 module is illustrated. K-means clustering algorithm 136 module receives clustering dataset 128 604 containing a plurality of unclassified cluster data entries 608 from clustering dataset 128. K-means clustering algorithm 136 module selects a k-value 612 where the k-value 612 reflects the number of classified data entry cluster 140 that will be generated by k-means clustering algorithm 136 module. K-means clustering algorithm 136 module may select a k-value 612 by classifying a therapeutic constitutional inquiry 112 as described above in more detail in reference to FIG. 1. K-means clustering algorithm 136 module may also select a k-value 612 by calculating distances from using Euclidean distance from K centroids as described above in more detail in FIG. 1. K-means clustering algorithm 136 module selects a k-value 612 of 5 and generates five classified data entry cluster 140 that include a first classified data entry cluster 140 616, a second classified data entry cluster 140 620, a third classified data entry cluster 140 624, a fourth classified data entry cluster 140 628, and a fifth classified data entry cluster 140 632. Each of the five classified data entry cluster 140 may contain one or more cluster data entries 636. In an embodiment, k-means clustering algorithm 136 module may generate a hard k-means clustering algorithm 136 wherein a cluster data entry 636 may be assigned to one classified data entry cluster 140. In such an instance, a cluster data entry 636 may only be assigned to fourth classified data entry cluster 140 628. In an embodiment, k-means clustering algorithm 136 module may generate a soft k-means clustering algorithm 136 wherein a cluster data entry 636 may be assigned to one or more classified data entry cluster 140. In such an instance, a cluster data entry 636 may be assigned to first classified data entry cluster 140 616, second classified data entry cluster 140 620, and fifth classified data entry cluster 140 632. K-means clustering algorithm 136 module calculates a degree of similarity index value that includes a measurement distance between a classified data entry cluster 140 and a user vibrancy datum 120 640. For example, k-means clustering algorithm 136 module may calculate a degree of similarity index value 644 between first classified data entry cluster 140 616 and user vibrancy datum 120 640. Similarly, k-means clustering algorithm 136 module may calculate a degree of similarity index value 648 between fifth classified data entry cluster 140 632 and user vibrancy datum 120 640. Similarity index may be calculated utilizing Euclidean distance as described above in more detail in reference to FIG. 1. In such an instance, k-means clustering algorithm 136 module may evaluate the distance and/or similarity index value between first classified data entry cluster 140 616 and user vibrancy datum 120 640 and the distance and/or similarity index value between fifth classified data entry cluster 140 632 and user vibrancy datum 120 640.

Figure 7:
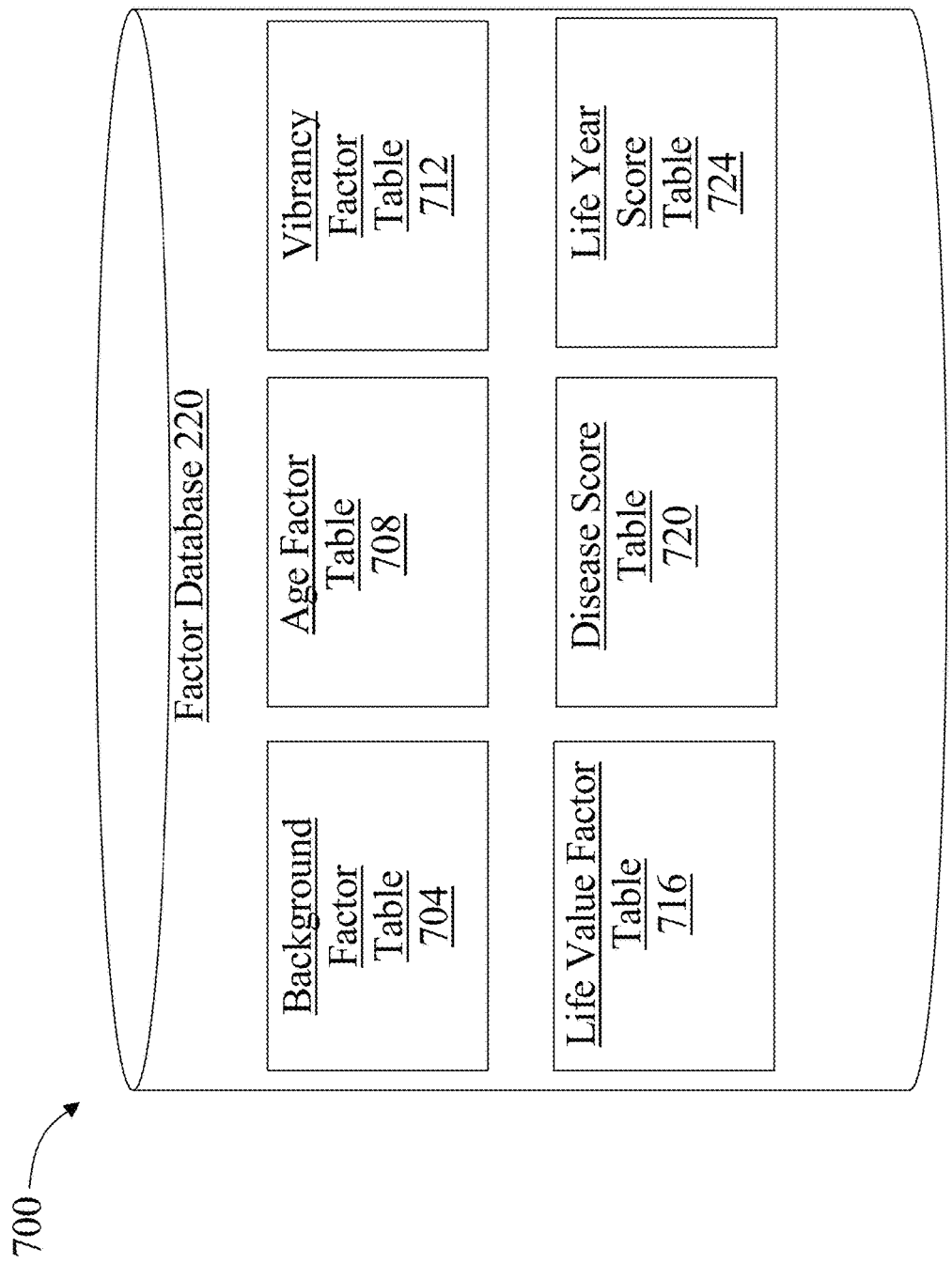
FIG. 7 is a block diagram illustrating an exemplary embodiment of a factor database.

Referring now to FIG. 7, an exemplary embodiment 700 of factor database is illustrated. Factor database may include any data structure suitable for use as vibrancy database 124. Factor database may include data utilized to calculate degree of similarity index value. One or more tables contained within factor database may include background factor table 704; background factor table 704 may include one or more data entries containing background factors. One or more tables contained within factor database may include age factor table 708; age factor table 708 may include one or more data entries containing age factors. One or more tables contained within factor database may include vibrancy factor table 712; vibrancy factor table 712 may include one or more data entries containing vibrancy factors. One or more tables contained within factor database may include life value factor table 716; life value factor table 716 may include one or more data entries containing life value factors. One or more tables contained within factor database may include disease score table 720; disease score table 720 may include one or more data entries containing disease scores. One or more tables contained within factor database may include life year score table 724; life year score table 724 may include one or more data entries containing life year scores.

Figure 8:
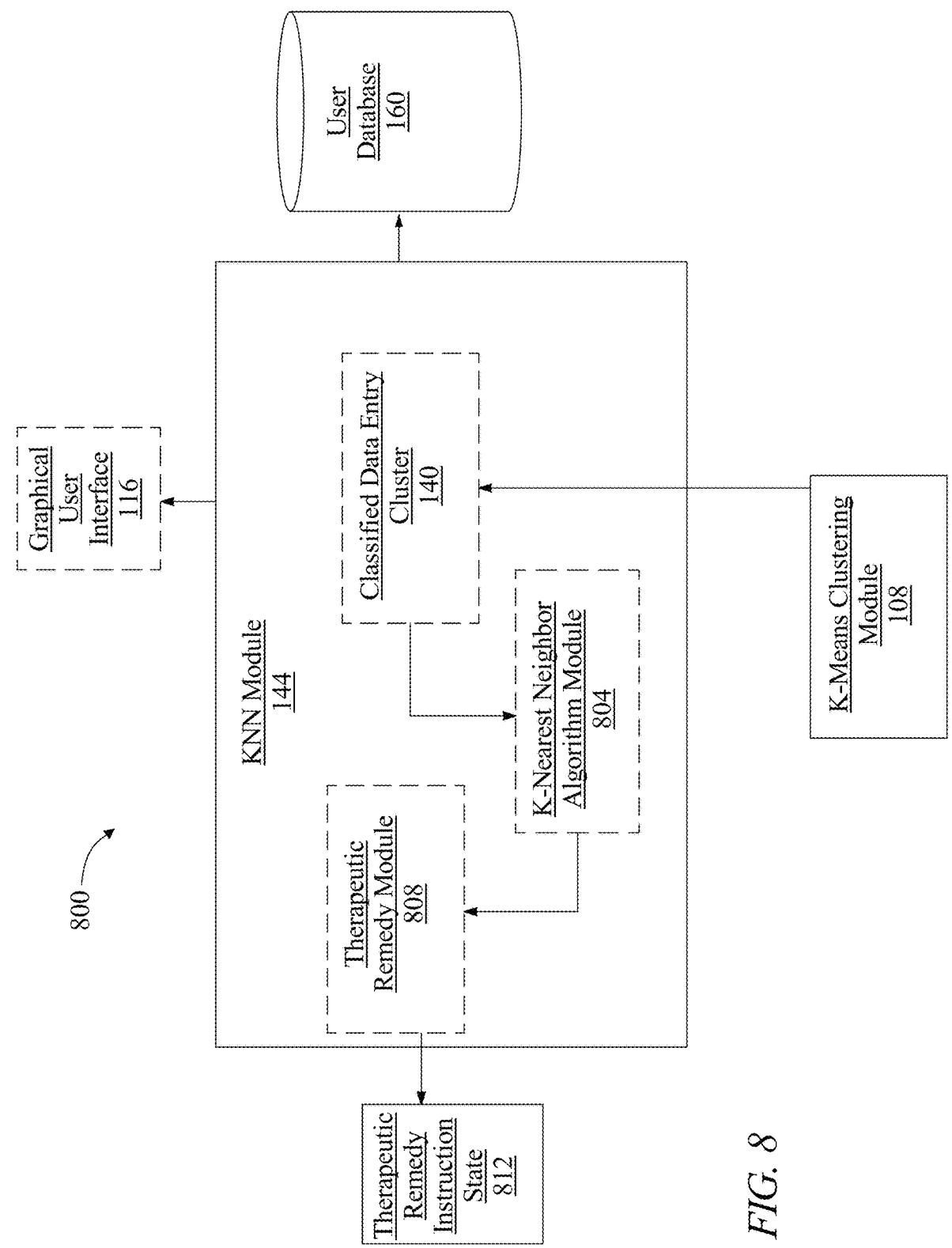
FIG. 8 is a block diagram illustrating an exemplary embodiment of a KNN module.

Referring now to FIG. 8, an exemplary embodiment of k-nearest neighbors (KNN) module is illustrated. KNN module may be implemented as a hardware or software module. KNN module is configured to receive from the K-means clustering module 108 the selected classified data entry cluster 140 and the at least a therapeutic constitutional inquiry 112; generate a k-nearest neighbors algorithm 152 utilizing the selected classified data entry cluster 140 and the at least a therapeutic constitutional inquiry 112; identify at least a therapeutic dataset contained within the selected classified data entry cluster 140 wherein the therapeutic dataset includes the at least a therapeutic constitutional inquiry 112 and a therapeutic remedy; generate a therapeutic remedy instruction set 156 as a function of identifying the therapeutic dataset; and display the therapeutic remedy instruction set 156 on a graphical user interface 116 located on the at least a computing device.

With continued reference to FIG. 8, KNN module receives classified data entry cluster 140 and therapeutic constitutional inquiry 112 selected by k-means clustering module 108. KNN module may receive classified data entry cluster 140 and therapeutic constitutional inquiry 112 utilizing any network methodology as described herein.

With continued reference to FIG. 8, KNN module may include K-nearest neighbors (KNN) algorithm module. KNN algorithm module may be implemented as a hardware or software module. KNN algorithm module generates a k-nearest neighbors algorithm 152 utilizing the selected classified data entry cluster 140 as training data and the at least a therapeutic constitutional inquiry 112. KNN algorithm module may calculate an optimal vector output for the at least a therapeutic constitutional inquiry 112 utilizing a k-nearest neighbors algorithm 152 and the selected classified data entry as training data. KNN algorithm module may modify selected classified data entry cluster 140 by representing selected classified data entry as vectors. Vectors may include mathematical representations of classified data entry cluster 140 training data. Vectors may include n-tuple of values which may represent a measurement or other quantitative value associated with a given category of data, or attribute. Vectors may be represented in n-dimensional space using an axis per category of value represented in n-tuple of values, such that a vector has a geometric direction characterizing the relative quantities of attributes in the n-tuple as compared to each other. In an embodiment, KNN module may calculate an initial heuristic ranking association between therapeutic constitutional inquiry 112 and elements of classified data entry cluster 140 training data. Initial heuristic may include selecting some number of highest-ranking associations and/or training data elements. KNN module may perform one or more processes to modify and/or format classified data entry cluster 140 training data. Classified data entry cluster 140 training data may contain "N" unique features, whereby a dataset contained within classified data entry cluster 140 training data and represented as a vector may contain a vector of length "N" whereby entry "I" of the vector represents that data point's value for feature "I." Each vector may be mathematically represented as a point in "R^N." For instance and without limitation, KNN module may modify entries contained within classified data entry cluster 140 training data to contain consistent forms of a variance. After appropriate selection of classified data entry cluster 140 training data by k-means clustering module 108, KNN module performs K-nearest neighbors algorithm 152 by classifying therapeutic datasets contained within the selected classified data entry cluster 140. Selected classified data entry cluster 140 training data may be represented as an "M×N" matrix where "M" is the number of data points contained within the classified data entry cluster 140 training data and "N" is the number of features contained within the selected classified data entry cluster 140 training data. Classifying datasets contained within selected classified data entry cluster 140 training data set may include computing a distance value between an item to be classified such as a therapeutic dataset and each dataset contained within selected classified data entry cluster 140 training set which may be represented as a vector. A value of "k" may be pre-determined or selected that will be used for classifications. In an embodiment, value of "k" may be selected as an odd number to avoid a tied outcome. In an embodiment, value of "k" may be decided by KNN module arbitrarily or value may be cross validated to find an optimal value of "k.". KNN module may then select a distance metric that will be used in K-nearest neighbors algorithm. In an embodiment, KNN module may utilize Euclidean distance which may be measure distance by subtracting the distance between a training data point and the datapoint to be classified such as therapeutic constitutional inquiry 112. In an embodiment, Euclidean distance may be calculated by a formula represented as: $E(x,y) = \sqrt{\sum_{i=0}^{n}(xi-yi)^2}$. In an embodiment, KNN module may utilize metric distance of cosine similarity which may calculate distance as the difference in direction between two vectors which may be represented as: $\text{similarity} = \cos\theta = A \times B \div \|A\|\|B\|$. After selection of "k" value, and selection of distance measurement by KNN module, KNN module may partition in "R^N" into sections. Sections may be calculated using the distance metric and the available data points contained within selected classified data entry cluster 140. KNN module may calculate a plurality of optimal vector outputs; in such an instance, where a plurality of matching entries is returned, optimal vector output may be obtained by aggregating matching entries including any suitable method for aggregation, including component-wise addition followed by normalization component-wise calculation of arithmetic means, or the like.

With continued reference to FIG. 8, KNN algorithm module identifies at least a therapeutic dataset contained within the selected classified data entry cluster 140 wherein the at least a therapeutic dataset includes a therapeutic constitutional inquiry 112 and a therapeutic remedy. Therapeutic remedy may include any of the therapeutic remedies as described above in more detail in reference to FIG. 1. KNN module may include a therapeutic remedy module 808 that may be implemented as a hardware or software module. Therapeutic remedy module 808 generates a therapeutic remedy instruction set 156 as a function of identifying a therapeutic dataset. Therapeutic remedy instruction set 156 includes any of the therapeutic remedy instruction set 156 as described above in reference to FIG. 1. Therapeutic remedy instruction may include one or more therapeutic remedies selected from one or more therapeutic datasets that have been utilized to treat the same therapeutic constitutional inquiry 112. For instance and without limitation, therapeutic remedy instruction set 156 may identify a particular medication that may be utilized to treat a user with cystic fibrosis. In yet another non-limiting example, therapeutic remedy instruction set 156 may identify a particular yoga sequence that has been utilized to treat a user with generalized anxiety disorder. Therapeutic remedy instruction set 156 may be utilized to identify treatments for diseases that may impact small communities of users or that may be newly created diseases with very little medical evidence available describing how to best treat users. Identification of other users who may have been diagnosed with the same medical condition and who may have had success with a particular treatment will help best optimize treatment and inform therapeutic professionals.

With continued reference to FIG. 8, KNN module displays therapeutic remedy instruction set 156 on a graphical user interface 116 located on computing device. Therapeutic professional who entered information about a particular therapeutic constitutional inquiry 112 may be able to view therapeutic remedy instruction set 156 and be informed about ways to optimize treatment for each patient. This may also help therapeutic professionals stay active and current with new treatments that may be available as it may be difficult for them to stay active with current medical literature and research. Having a system that incorporates this information into their practice may help streamline and optimize medical treatment.

With continued reference to FIG. 8, KNN module may include a user database 160. User database 160 may be implemented as any data structure suitable for use as vibrancy database 124. User database 160 may include one or more entries regarding a user that may be utilized by KNN module to filter particular therapeutic remedies contained within therapeutic remedy instruction set 156. For example, KNN module may consult user database 160 to determine a user's allergies to medication to ensure a medication that a user is allergic to is not included in therapeutic dataset as described in more detail below.

Figure 9:
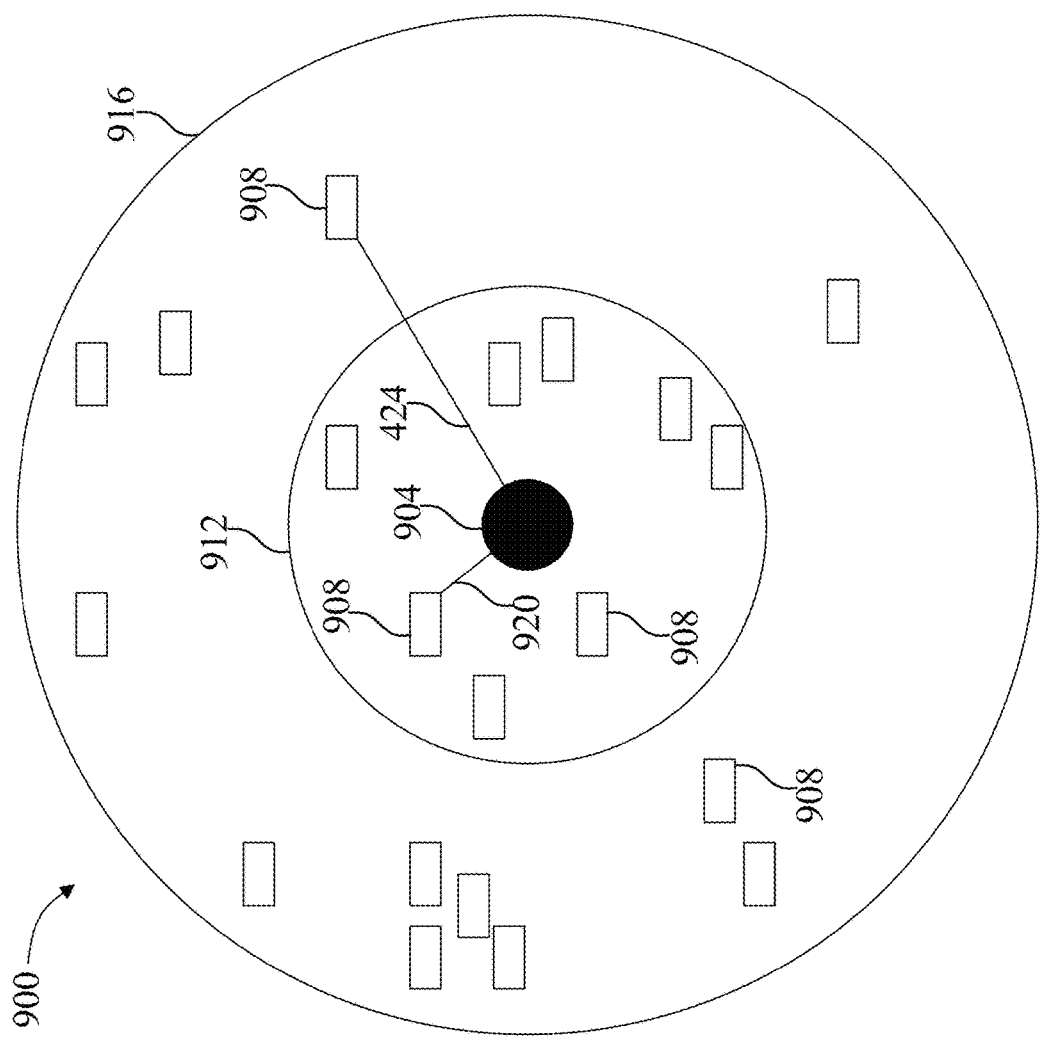
FIG. 9 is a diagrammatic representation of a K-nearest neighbors algorithm.

Referring now to FIG. 9, an exemplary embodiment 900 of k-nearest neighbors algorithm 152 is illustrated. Embodiment 904 represents a therapeutic constitutional inquiry 112 to be classified. Embodiment 908 represents data sets from selected classified data entry cluster 140. Embodiment 908 may be represented as "m" number of datasets contained within selected classified data entry cluster 140. Embodiment 912 indicates a first "k" value selected, and the corresponding number of datasets contained utilizing first "k" value. Embodiment 916 indicate a second "k" value selected and the corresponding number of datasets contained utilizing second "k" value. Embodiment 920 represents distance between therapeutic constitutional inquiry 112 to be classified embodiment 904 and a particular dataset from selected classified data entry cluster 140 embodiment 908. Embodiment 920 represents distance between therapeutic constitutional inquiry 112 to be classified embodiment 904 and a particular dataset from selected classified data entry cluster 140 embodiment 908. Distance may be measured utilizing any of the methodologies as described above in reference to FIG. 1 and FIG. 8, including for example Euclidean distance and/or cosine similarity.

Figure 10:
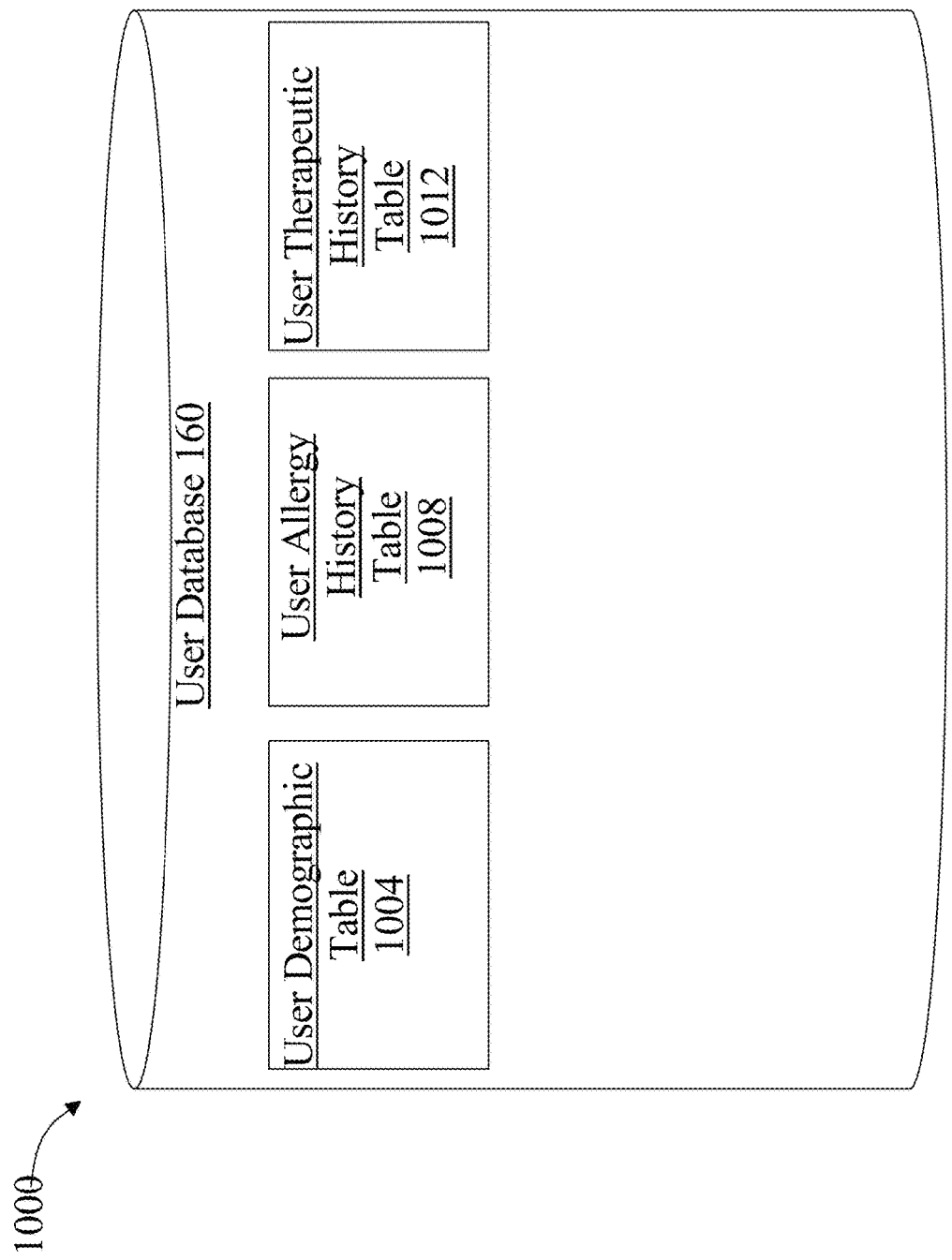
FIG. 10 is a block diagram illustrating an exemplary embodiment of a user database.

Referring now to FIG. 10, an exemplary embodiment 1000 of user database 160 is illustrated. User database 160 may be implemented as any data structure suitable for use as vibrancy database 124 as described above in more detail in reference to FIG. 1. One or more tables contained within user database 160 may include user demographic table 1004; user demographic table 1004 may include one or more data entries describing demographic information regarding a particular user. One or more tables contained within user database 160 may include user allergy history table 1008; user allergy history table 1008 may include one or more data entries describing a user's allergy history to medications, supplements, foods, chemicals, household products, and the like. One or more tables contained within user database 160 may include user therapeutic history table 1012; user therapeutic history table 1012 may include one or more data entries describing previous therapeutic remedies that a user may have utilized in the past including therapeutic remedies that were beneficial to a user and therapeutic remedies that were not beneficial to a user.

Figure 11:
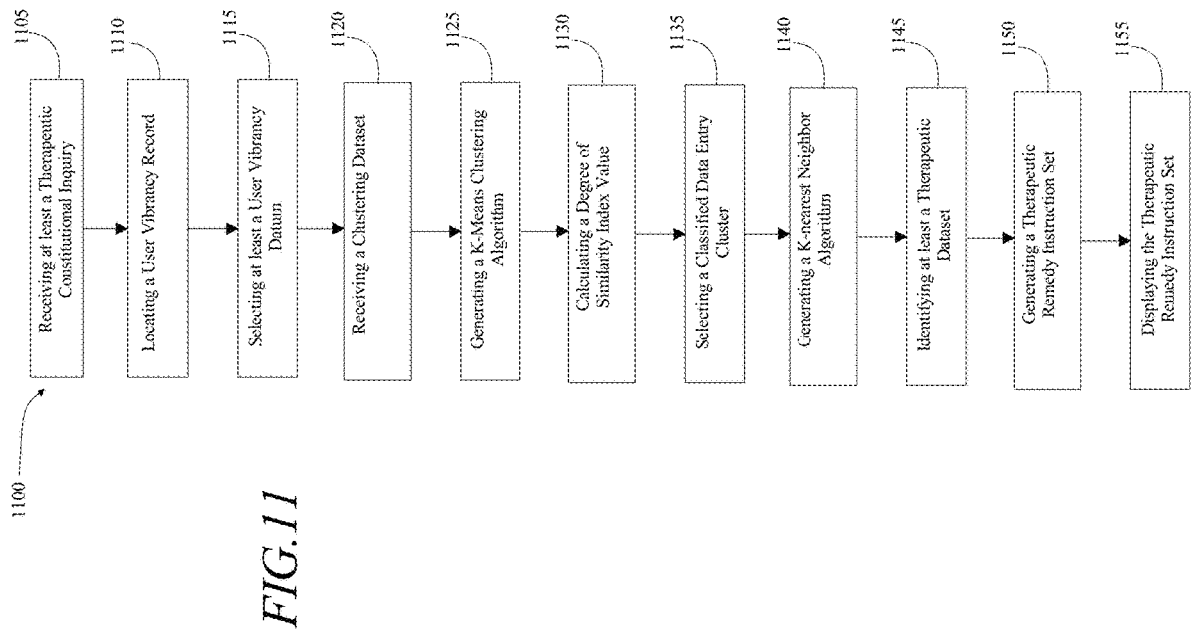
FIG. 11 is a process flow diagram illustrating an exemplary embodiment of a method of locating therapeutic remedies.

Referring now to FIG. 11, an exemplary embodiment of a method 1100 of locating therapeutic remedies is illustrated. At step 1105 at least a computing device receives at least a therapeutic constitutional inquiry 112 input from a graphical user interface 116 by a therapeutic professional. Computing device may include any of the computing devices as described herein. At least a therapeutic constitutional inquiry 112 may include any of the therapeutic constitutional inquires as described above in reference to FIGS. 1-11. In an embodiment, at least a therapeutic constitutional inquiry 112 may include a current diagnosed medical condition such as human immunodeficiency virus (HIV) or hypothyroidism. At least a therapeutic constitutional inquiry 112 includes a user identifier. User identifier may include any of the user identifiers as described above in reference to FIGS. 1-10. Graphical user interface 116 may include any of the graphical user interface 116 as described above in reference to FIGS. 1-11. In an embodiment, graphical user interface 116 may include a drop down menu where a therapeutic professional may select a therapeutic constitutional inquiry 112 from a list. In an embodiment, graphical user interface 116 may include a free form textual entry field where a therapeutic professional may type in a therapeutic constitutional inquiry 112. Therapeutic professional may include any of the therapeutic professionals as described above in reference to FIGS. 1-11. Computing device may receive at least a therapeutic constitutional inquiry 112 using any of the network methodologies as described above in reference to FIGS. 1-11.

With continued reference to FIG. 11, at step 1110 at least a computing device locates a user vibrancy record containing a plurality of user vibrancy datum 120 stored in a vibrancy database 124 as a function of the user identifier. User vibrancy record may include any of the user vibrancy records as described above in reference to FIGS. 1-11. User vibrancy record may include a plurality of user vibrancy datum 120 that may contain stored information relating to a user's medical chart including for example clinical data, lab results, immunizations, medications, and the like. User vibrancy record may be stored in vibrancy database 124 as described above in more detail in reference to FIG. 1 and FIG. 4. Computing device may locate a user vibrancy database 124 utilizing user identifier received with user constitutional inquiry. In an embodiment, at least a computing device may compare a user identifier contained within a therapeutic constitutional inquiry 112 to a user identifier located within vibrancy database 124.

With continued reference to FIG. 11, at step 1115 at least a computing device selects at least a user vibrancy datum 120 as a function of at least a therapeutic constitutional inquiry 112. At least a computing device may select at least a user vibrancy datum 120 that may be related and/or relevant to at least a therapeutic constitutional inquiry 112. For instance and without limitation, at least a computing device may select at least a user vibrancy datum 120 that includes a blood test showing elevated triglycerides for a therapeutic constitutional inquiry 112 such as stage one heart disease. In yet another non-limiting example, at least a computing device may select at least a user vibrancy datum 120 such as a genetic analysis showing a mutation to on PKD1 allele on chromosome 16 showing an increased susceptibility to develop polycystic kidney disease for a user with a therapeutic constitutional inquiry 112 that includes acute kidney disease. In an embodiment, computing device may select at least a user vibrancy datum 120 based on expert input as described above in more detail in reference to FIG. 3. In an embodiment, computing device may select at least a user vibrancy datum 120 based on learned associations between therapeutic constitutional inquiries and user vibrancy datum 120 such as by vibrancy learner 208 as described above in more detail in reference to FIG. 2.

With continued reference to FIG. 11, at step 1120 at least a computing device receives a clustering dataset 128 wherein the clustering dataset 128 includes a plurality of unclassified cluster data entries. Clustering dataset 128 may include any of the clustering dataset 128 as described above in more detail in reference to FIGS. 1-11. Clustering dataset 128 includes unclassified cluster data entries as described above in more detail in reference to FIGS. 1-11. At least a computing device receives clustering dataset 128 from clustering database 132 as described above in more detail in reference to FIG. 5. In an embodiment, clustering dataset 128 may be stored within clustering database 132 based on categorizations by demographics contained within clustering dataset 128, medical conditions contained within clustering dataset 128, vibrancy datums contained within clustering dataset 128, and/or therapeutic remedies contained within clustering dataset 128 as described above in more detail in reference to FIG. 5.

With continued reference to FIG. 11, at step 1125 at least a computing device generates a k-means clustering algorithm 136 using the clustering dataset 128 containing the plurality of cluster data entries containing unclassified data as input. K-means clustering algorithm 136 includes any of the k-means clustering algorithm 136 as described above in reference to FIGS. 1-11. K-means clustering algorithm 136 outputs a definite number of classified data entry cluster 140 wherein the classified data entry cluster 140 each contain cluster data entries. Computing device may determine k-value or definite number of classified data entry cluster 140 by evaluating therapeutic constitutional inquiry 112 to determine a constitutional classifier and selecting a definite number of classified data entry cluster 140 as a function of the constitutional classifier. In an embodiment, constitutional classifier may include classifying constitutional inquiry utilizing any of the classifiers as described above. This may include classifying constitutional inquiry by location of where a medical condition impacts a person's body or the pathology of a particular medical condition. Generating k-means clustering algorithm 136 may include generating a hard k-means clustering algorithm 136 wherein a cluster data entry is selected to be assigned to one cluster of the definite number of classified data entry cluster 140. Generating k-means clustering algorithm 136 may include generating a soft k-means clustering algorithm 136 wherein a cluster data entry is selected to be assigned to multiple clusters of the definite number of classified data entry cluster 140.

With continued reference to FIG. 11, at step 1130 at least a computing device calculates a degree of similarity index value. At least a computing device calculates a degree of similarity index value utilizing any of the methods as described above in reference to FIGS. 1-11. Degree of similarity index value includes a distance measurement between a classified data entry cluster 140ing and at least a selected user vibrancy datum 120. Distance may be measured utilizing Euclidean distance as described above in reference to FIGS. 1-11. Degree of similarity index value may include a formula that includes a background factor multiplied by an age factor and a vibrancy factor and divided by a life value factor. Disease factor may include a disease score multiplied by a life year score as described above in more detail in reference to FIG. 7. Factors utilized to calculate degree of similarity index value may be calculated utilizing any of the factors contained within factor database as described above in more detail in reference to FIG. 7.

With continued reference to FIG. 11, at step 1135 at least a computing device selects a classified data entry cluster 140 as a function of the degree of similarity index value. At least a computing device may evaluate degree of similarity calculated for each of the classified data entry cluster 140. This may be performed utilizing any of the methods as described above in reference to FIGS. 1-11.

With continued reference to FIG. 11, at step 1140 at least a computing device generates a k-nearest neighbors algorithm 152 utilizing the selected classified data entry cluster 140 and the at least a therapeutic constitutional inquiry 112. Generating k-nearest neighbors algorithm 152 may be performed utilizing any of the methodologies as described above in reference to FIGS. 1-11. Generating k-nearest neighbors algorithm 152 may include generating a first vector output containing a data entry cluster, generating a second vector output containing at least a therapeutic constitutional inquiry 112 and calculating the distance between the first vector output and the second vector output utilizing Euclidean distance measurement. This may be performed utilizing any of the methods as described above in reference to FIGS. 1-11. Generating k-nearest neighbors algorithm 152 may include generating an optimal vector output as a function of distance between a first vector output and a second vector output and identifying a therapeutic dataset utilizing the optimal vector output.

With continued reference to FIG. 11, at step 1145 at least a computing device identifies at least a therapeutic dataset contained within a selected classified data entry cluster 140 wherein the therapeutic dataset includes at least a therapeutic constitutional inquiry 112 and a therapeutic remedy. Therapeutic remedy may include any of the therapeutic remedies as described above in reference to FIGS. 1-11. Therapeutic dataset may be identified as a function of generating k-nearest neighbors algorithm.

With continued reference to FIG. 11, at least a computing device generates a therapeutic remedy instruction set 156. Therapeutic remedy instruction set 156 includes any of the therapeutic remedy instruction set 156 as described above in reference to FIGS. 1-11. Therapeutic remedy instruction set 156 may include a therapeutic remedy identified from therapeutic dataset.

With continued reference to FIG. 11, at least a computing device displays a therapeutic remedy instruction set 156 on a graphical user interface 116 located on at least a computing device. This may be performed utilizing any of the methods as described above in reference to FIGS. 1-11.

Figure 12:
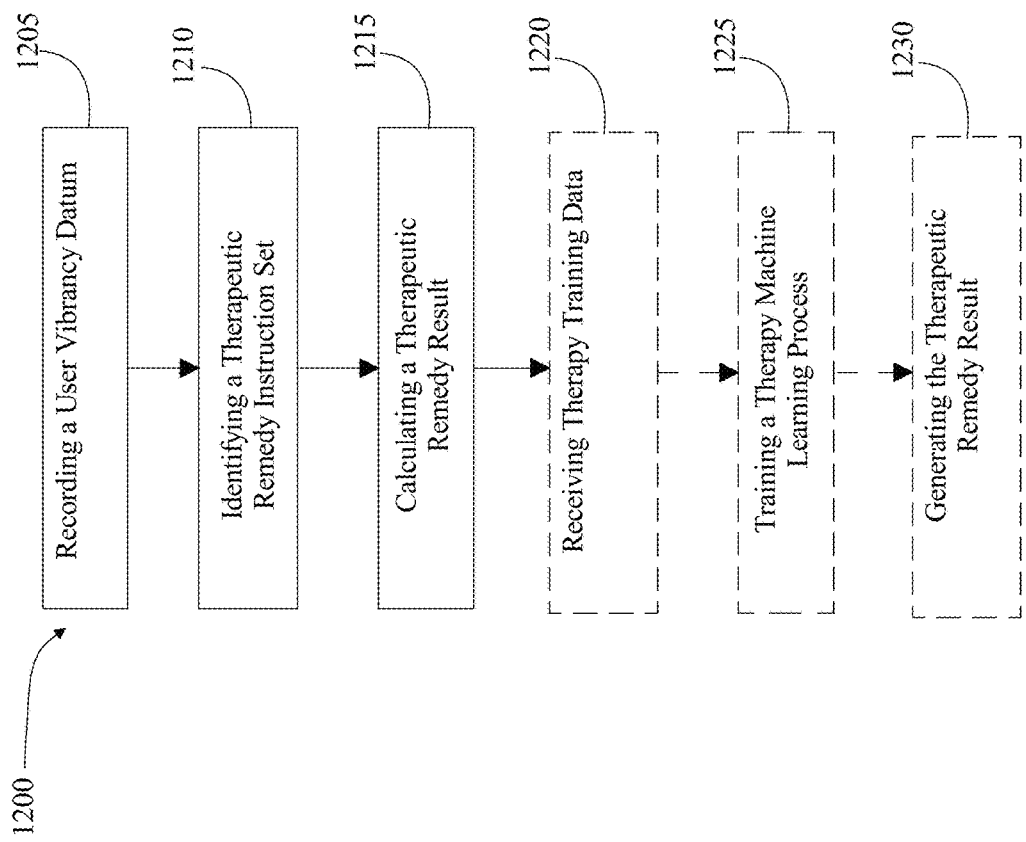
FIG. 12 is a process flow diagram illustrating an exemplary embodiment of a method of calculating a therapeutic remedy result.

Referring now to FIG. 12, an exemplary embodiment 1200 of a method of calculating a therapeutic remedy result is illustrated. At step 1205, computing device 104 records a user vibrancy datum 120. User vibrancy datum 120 includes any of the user vibrancy datums 120 as described above in more detail in reference to FIGS. 1-11. Once recorded, a user vibrancy datum 120 may be stored within vibrancy database 124. Computing device 104 may record a user vibrancy datum 120 at timed intervals, such as a heart rate which may be measured and recorded three times per day, or a user's sleep pattern which may be measured and recorded nightly.

With continued reference to FIG. 12, computing device 104 retrieves a user vibrancy record. A user vibrancy record includes any of the user vibrancy records as described above in more detail in reference to FIGS. 1-11. Computing device 104 identifies a therapeutic indication contained within a user vibrancy record and selects a user vibrancy datum 120 to record as a function of the therapeutic indication. For instance and without limitation, computing device 104 may identify a therapeutic indication such as hypertension, whereby computing device 104 selects a user vibrancy datum 120 such as blood pressure to record. In yet another non-limiting example, computing device 104 may identify a therapeutic indication such as anxiety, whereby computing device 104 selects a user vibrancy datum 120 such as heart rate variability to record. Computing device 104 identifies an environmental indicator relating to a user vibrancy datum. An environmental indicator includes any of the environmental indicators as described above in more detail in reference to FIGS. 1-11. Computing device 104 records an environmental indicator relating to a user vibrancy datum. For example, computing device 104 may identify an environmental indicator such as a user who experiences a migraine after consuming red wine. In yet another non-limiting example, computing device 104 may identify an environmental indicator such as a user who experiences an episode of vertigo after the user traveled to a location with different altitude.

With continued reference to FIG. 12, at step 1210, computing device 104 identifies a therapeutic remedy instruction set 156 as a function of a user vibrancy datum. A therapeutic remedy instruction set, includes any of the therapeutic remedy instruction sets as described above in more detail in reference to FIGS. 1-11. A therapeutic remedy instruction set contains a therapeutic remedy. A therapeutic remedy includes any of the therapeutic remedies as described above in more detail in reference to FIGS. 1-11. Therapeutic remedy instruction set 156 contains one or more therapeutic remedies utilized to treat the same therapeutic constitutional inquiry 112. For instance and without limitation, therapeutic remedy instruction set 156 may contain a recommendation for a user to consume three servings of monounsaturated fats each day, to aid in raising a user's high density lipoprotein (HDL) levels. In yet another non-limiting example, therapeutic remedy instruction set 156 may contain a remedy such as a meditation sequence that a user is recommended to practice three nights each week based on a user's therapeutic constitutional inquiry 112 of anxiety.

With continued reference to FIG. 12, at step 1215, computing device 104 calculates a therapeutic remedy result that associates a user vibrancy datum 120 and a therapeutic remedy with a therapy response curve. A therapy response curve contains any of the therapy response curves as described above in more detail in reference to FIGS. 1-11. Computing device 104 generates a response label as a function of a therapy response curve and displays a response label. A response label includes any of the response labels as described above in more detail in reference to FIGS. 1-11. A response label may contain feedback generated using a therapy response curve. For example, a response label may contain remarks and/or feedback for a user relating to a therapy response curve. For instance and without limitation, a response label may contain a motivational reply, to encourage a user to continue to stick with the user's exercise regimen. In yet another non-limiting example, a response label may tell a user to slow down, and not to practice too much yoga, because the user is over-exercising. Response label may be displayed to a user on display 168. Computing device 104 displays an alert when a response label comes below a threshold parameter. A threshold parameter includes any of the threshold parameters as described above in more detail in reference to FIGS. 1-11. In an embodiment, a threshold parameter may be determined and/or pre-selected by a user and/or a user's medical doctor. For example, a user may specify that the user wishes to be alerted when the user's blood glucose level falls below 60 milligrams per deciliter. An alert includes any of the alerts as described above in more detail. For example, an alert may include an auditory alert such as an alarm. In yet another non-limiting example, an alert may include a visual alert, such as a warning sign that is displayed to a user.

With continued reference to FIG. 12, at step 1220, computing device 104 receives therapy training data. Therapy training data includes a plurality of data entries containing user vibrancy datums and therapeutic remedy instruction sets correlated to therapeutic remedy results. Therapy training data may be obtained from one or more sources including but not limited to, expert inputs, previous iterations of calculating therapeutic remedy results, scientific articles, journals, publications, and the like.

With continued reference to FIG. 12, at step 1225, computing device 104 trains a therapy machine learning process using therapy training data. Therapy machine-learning process includes any of the machine-learning processes as described above in more detail in reference to FIGS. 1-11. Therapy machine-learning process uses a user vibrancy datum and a therapeutic remedy as an input, and outputs a therapy response curve and a therapeutic remedy result.

With continued reference to FIG. 12, at step 1230, computing device 104 generates a therapeutic remedy result as a function of training therapy machine-learning process. Computing device 104 records a first user vibrancy datum relating to an event. For example, a first user vibrancy datum such as a user's blood pressure may be recorded while the user sleeps, the night before the user is set to take a major examination. Computing device 104 establishes a user's response as a function of the first user vibrancy datum. For example, computing device may establish that a user's blood pressure increased the night before the user was set to take a major examination. Computing device 104 identifies a user response as a function of a second user vibrancy datum, and displays a message relating to an event. For example, a subsequent spike in blood pressure as recorded by a second user vibrancy datum, may prompt computing device 104 to display a message, alerting the user to the increase in blood pressure.

With continued reference to FIG. 12, computing device 104 locates information relating a user's program. A user's program may include any scheduling and/or calendar information relating to a user. Computing device 104 identifies an opening contained within a user's program. An opening may occur when a user has free time and can accommodate scheduling an activity and/or appointment that may relate to a therapeutic remedy instruction set. Computing device 104 creates an entry relating to a therapeutic remedy instruction set. For example, computing device 104 may locate information relating to a user's schedule and identify a two hour time block when the user is available. In such an instance, computing device 104 may create an entry relating to a user's therapeutic remedy instruction set 156 and schedule the user to practice yoga for fifteen minutes during the two hour time block when the user is available. Computing device 104 records a user vibrancy datum 120 during an entry and generates a completion index as a function of the user vibrancy datum 120. A completion index indicates what portion of a therapeutic remedy was completed during a specified time. Computing device 104 displays a response relating to a completion index. For instance and without limitation, computing device 104 may provide words of encouragement and support for a user if a completion index reflects that a user only completed a portion of the user's exercise regimen. In yet another non-limiting example, computing device 104 may congratulate the user if a completion index reflects that the user fully completed a vigorous exercise regimen as contained within a therapeutic remedy instruction set 156. Computing device 104 inserts a user vibrancy datum 120 and a therapeutic remedy instruction set 156 into a user vibrancy record and updates a user vibrancy record. This may allow for periodic and real time updating of a user vibrancy record. In an embodiment, a user may be able to access a user vibrancy record from wearable device 164.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
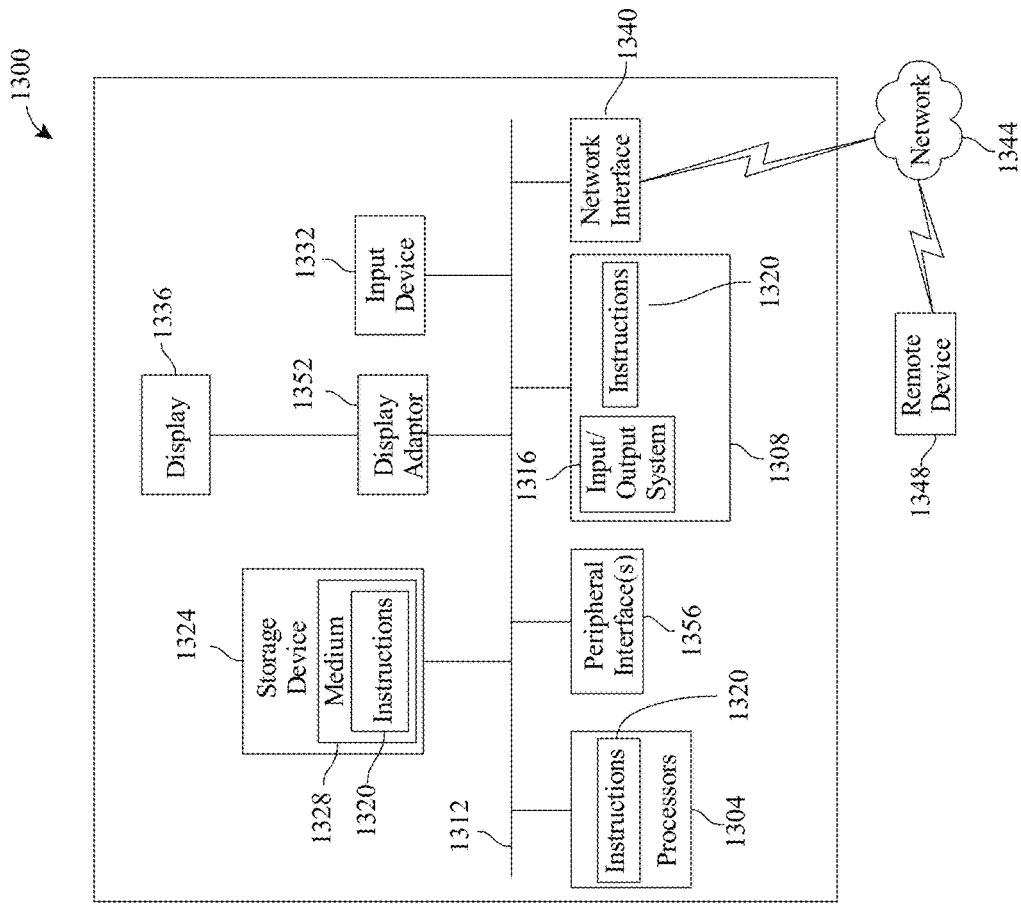
FIG. 13 is a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1313. Bus 1313 may include any of several types of bus structures including, but not limited to, a memory bus, a memory controller, a peripheral bus, a local bus, and any combinations thereof, using any of a variety of bus architectures.

Memory 1308 may include various components (e.g., machine-readable media) including, but not limited to, a random access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media)

instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1313 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1313 via any of a variety of interfaces (not shown) including, but not limited to, a serial interface, a parallel interface, a game port, a USB interface, a FIREWIRE interface, a direct interface to bus 1313, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1313 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A wearable device for calculating a therapeutic remedy result, the device comprising:
   a display;
   a sensor; and
   a computing device in communication with the display and the sensor, wherein the computing device is further configured to:
   record, using the sensor, a user vibrancy datum;
   identify a therapeutic remedy instruction set as a function of the user vibrancy datum, wherein the therapeutic remedy instruction set comprises a therapeutic remedy; and
   calculate a therapeutic remedy result that associates the user vibrancy datum and the therapeutic remedy with a therapy response curve; wherein calculating the therapeutic remedy result further comprises:

receiving therapy training data, wherein therapy training data further comprises a plurality of data entries containing user vibrancy datums and therapeutic remedy instruction sets correlated to therapeutic remedy results;

iteratively training a therapy machine learning process using the therapy training data, wherein the therapy machine learning process uses the user vibrancy datum and the therapeutic remedy as an input, and outputs a therapy response curve and a therapeutic remedy result, wherein training the therapy machine learning process using the therapy training data improves generation of therapeutic remedy results from the therapy machine learning process;

generating the therapeutic remedy result as a function of training the therapy machine learning process;

generating a response label as a function of the therapy response curve, wherein the response label includes feedback in relation to the therapy response curve; and display the therapeutic remedy instruction set, therapy response curve, and response label on a graphical user interface located on the at least a computing device.

2. The device of claim 1, wherein the computing device is further configured to:
record the user vibrancy datum at a timed interval.

3. The device of claim 1, wherein the computing device is further configured to:
retrieve a user vibrancy record;
identify a therapeutic indication contained within the user vibrancy record; and
select a user vibrancy datum to record as a function of the therapeutic indication.

4. The device of claim 3, wherein the computing device is further configured to:
identify an environmental indicator relating to the user vibrancy datum; and
record the environmental indicator relating to the user vibrancy datum.

5. The device of claim 1, wherein the computing device is further configured to:
generate a response label as a function of the therapy response curve; and
display the response label.

6. The device of claim 5, wherein the computing device is further configured to display an alert when the response label comes below a threshold parameter.

7. The device of claim 1, wherein the computing device is further configured to:
record a first user vibrancy datum relating to an event;
establish a user response as a function of the first user vibrancy datum;
identify the user response as a function of a second user vibrancy datum; and
display a message relating to the event.

8. The device of claim 1, wherein the computing device is further configured to:
locate information relating to a user's program;
identify an opening contained within the user's program; and
create an entry relating to the therapeutic remedy instruction set.

9. The device of claim 8, wherein the computing device is further configured to:
record the user vibrancy datum during the entry;
generate a completion index as a function of the user vibrancy datum; and
display a response relating to the completion index.

10. The device of claim 1, wherein the computing device is further configured to:
insert the user vibrancy datum and the therapeutic remedy instruction set into a user vibrancy record; and
update the user vibrancy record as a function of inserting the user vibrancy datum and the therapeutic remedy instruction set.

11. A method of calculating a therapeutic remedy result, the method comprising:
recording by a wearable device, a user vibrancy datum;
identifying by the wearable device, a therapeutic remedy instruction set as a function of the user vibrancy datum, wherein the therapeutic remedy instruction set comprises a therapeutic remedy; and
calculating by the wearable device, a therapeutic remedy result that associates the user vibrancy datum and the therapeutic remedy with a therapy response curve;
wherein calculating the therapeutic remedy result further comprises:
receiving therapy training data, wherein therapy training data further comprises a plurality of data entries containing user vibrancy datums and therapeutic remedy instruction sets correlated to therapeutic remedy results;
iteratively training a therapy machine learning process using the therapy training data, wherein the therapy machine learning process uses the user vibrancy datum and the therapeutic remedy as an input, and outputs a therapy response curve and a therapeutic remedy result, wherein training the therapy machine learning process using the therapy training data improves generation of therapeutic remedy results from the therapy machine learning process;
generating the therapeutic remedy result as a function of training the therapy machine learning process; and
generating a response label as a function of the therapy response curve, wherein the response label includes feedback in relation to the therapy response curve; and
displaying the therapeutic remedy instruction set, therapy response curve, and response label on a graphical user interface located on the at least a computing device.

12. The method of claim 11, wherein recording the user vibrancy datum further comprises recording the user vibrancy datum at a timed interval.

13. The method of claim 11, wherein identifying the therapeutic remedy instruction set further comprises:
retrieving a user vibrancy record;
identifying a therapeutic indication contained within the user vibrancy record; and
selecting a user vibrancy datum to record as a function of the therapeutic indication.

14. The method of claim 13 further comprising:
identifying an environmental indicator relating to the user vibrancy datum; and
recording the environmental indicator relating to the user vibrancy datum.

15. The method of claim 11, wherein calculating the therapeutic remedy result further comprises:
generating a response label as a function of the therapy response curve; and
displaying the response label.

16. The method of claim 15 further comprising displaying an alert when the response label comes below a threshold parameter.

17. The method of claim 11, wherein calculating the therapeutic remedy result further comprises:
- recording a first user vibrancy datum relating to an event;
- establishing a user response as a function of the first user vibrancy datum;
- identifying the user response as a function of a second user vibrancy datum; and
- displaying a message relating to the event.

18. The method of claim 11, wherein calculating the therapeutic remedy result further comprises:
- locating information relating to a user's program;
- identifying an opening contained within the user's program; and
- creating an entry relating to the therapeutic remedy instruction set.

19. The method of claim 18 further comprising:
- recording the user vibrancy datum during the entry;
- generating a completion index as a function of the user vibrancy datum; and
- displaying a response relating to the completion index.

20. The method of claim 11 further comprising:
- inserting the user vibrancy datum and the therapeutic remedy instruction set into a user vibrancy record; and
- updating the user vibrancy record as a function of inserting the user vibrancy datum and the therapeutic remedy instruction set.

* * * * *